(12) United States Patent
O'Dea et al.

(10) Patent No.: US 8,756,806 B2
(45) Date of Patent: Jun. 24, 2014

(54) CATHETER AND A METHOD FOR PRODUCING A CATHETER

(75) Inventors: John O'Dea, Bearna (IE); Adrian McHugh, Kilcolgen (IE); Patrick Griffin, Castlegar (IE)

(73) Assignee: Flip Technologies Limited, Galway (IE)

( * ) Notice: Subject to any disclaimer, the term of this patent is extended or adjusted under 35 U.S.C. 154(b) by 974 days.

(21) Appl. No.: 12/665,450

(22) PCT Filed: Jun. 27, 2008

(86) PCT No.: PCT/IE2008/000069
§ 371 (c)(1),
(2), (4) Date: Mar. 17, 2010

(87) PCT Pub. No.: WO2009/001327
PCT Pub. Date: Dec. 31, 2008

(65) Prior Publication Data
US 2010/0228202 A1 Sep. 9, 2010

(30) Foreign Application Priority Data

Jun. 27, 2007 (IE) .................................. S2007/0464
Nov. 19, 2007 (IE) .................................. S2007/0842

(51) Int. Cl.
*H01R 43/02* (2006.01)
(52) U.S. Cl.
USPC ............... 29/860; 29/857; 29/825; 29/592.1; 156/47; 156/60; 156/188; 604/264; 604/19; 604/48

(58) Field of Classification Search
USPC ............ 29/825, 592, 592.1; 156/47, 60, 188; 604/264, 19, 48
See application file for complete search history.

(56) References Cited

U.S. PATENT DOCUMENTS 5,199,433 A * 4/1993 Metzger et al. ............... 600/380
5,215,089 A * 6/1993 Baker, Jr. ....................... 600/377
(Continued)

FOREIGN PATENT DOCUMENTS

EP 0647435 A1 4/1995
WO 9949932 A1 10/1999

OTHER PUBLICATIONS

International Search Report for PCT/IE2008/000069 Jan. 5, 2009.

*Primary Examiner* — Peter DungBa Vo
*Assistant Examiner* — Azm Parvez
(74) *Attorney, Agent, or Firm* — Sughrue Mion, PLLC

(57) ABSTRACT

A method for producing a catheter (100) having a plurality of axially spaced apart electrodes (5) towards a distal end (4) of the catheter (100) comprises forming the electrodes (5) from a single sheet (110) of electrically conductive foil material by forming spaced apart slots (111) in the sheet material to define a plurality of spaced apart electrically conductive elements (114) extending transversely between spaced apart elongated connecting portion (112,113). The electrically conductive elements (114) subsequently form the electrodes (5), and are retained spaced apart by the connecting portions (112,113) until bonded to the catheter (100). Electrically conductive wires (10) electrically coupled to the electrically conductive elements (114) extend through an elongated slot (105) into and along an axial communicating bore (9) to a proximal end (3) of the catheter (100). Two pieces of double-sided adhesive tape (118) bonded to the electrically conductive elements (114) in turn bond the electrically conductive elements (114) to the catheter (100). After entering the wires (10) into the axial communicating bore (9) the electrically conductive elements (114) with the double-sided tape (118) are wrapped around the catheter (100) and are severed from the connecting portions (112,113). Free ends (115) of the electrically conductive elements (114) abut each other to form the electrodes (5) as band electrodes.

20 Claims, 11 Drawing Sheets

(56) References Cited

U.S. PATENT DOCUMENTS

Figure 3:
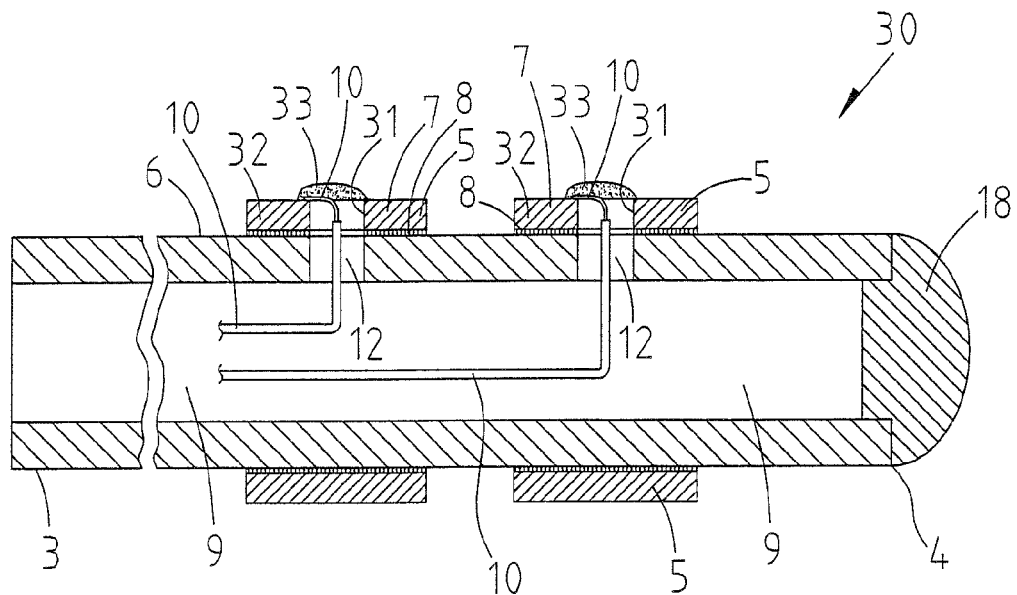

| | | | |
|---|---|---|---|
| 5,417,208 A * | 5/1995 | Winkler | 600/374 |
| 5,857,997 A * | 1/1999 | Cimino et al. | 604/95.01 |
| 2001/0003798 A1 * | 6/2001 | McGovern et al. | 606/41 |

* cited by examiner

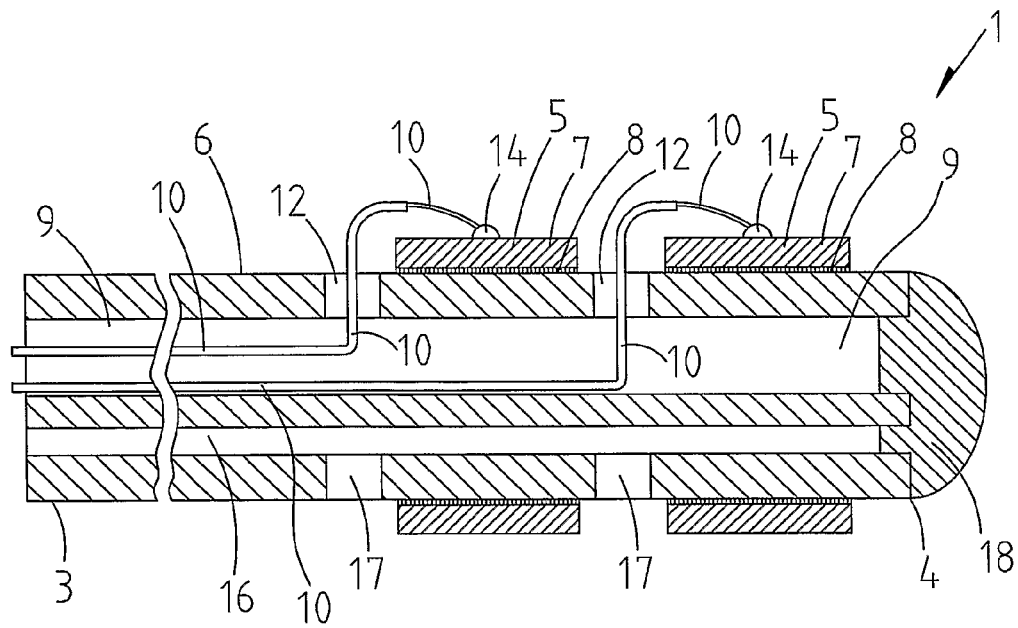
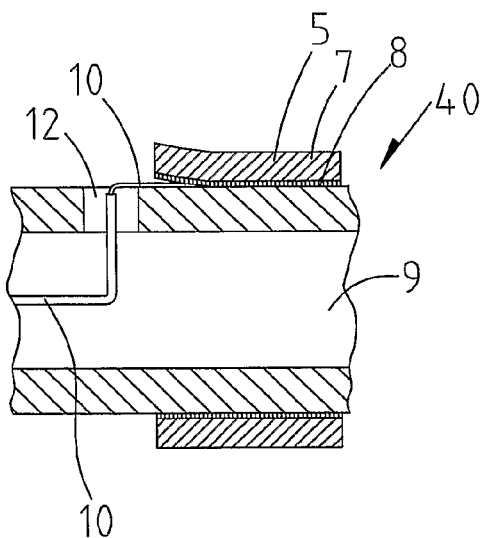 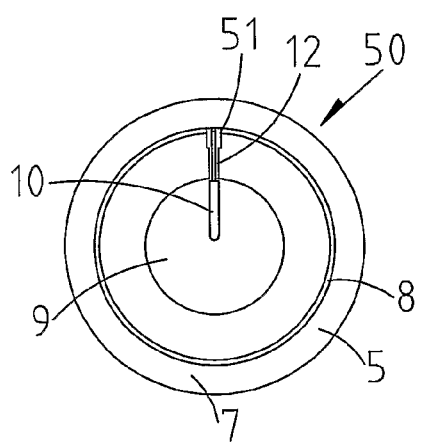
Fig. 4  Fig. 6

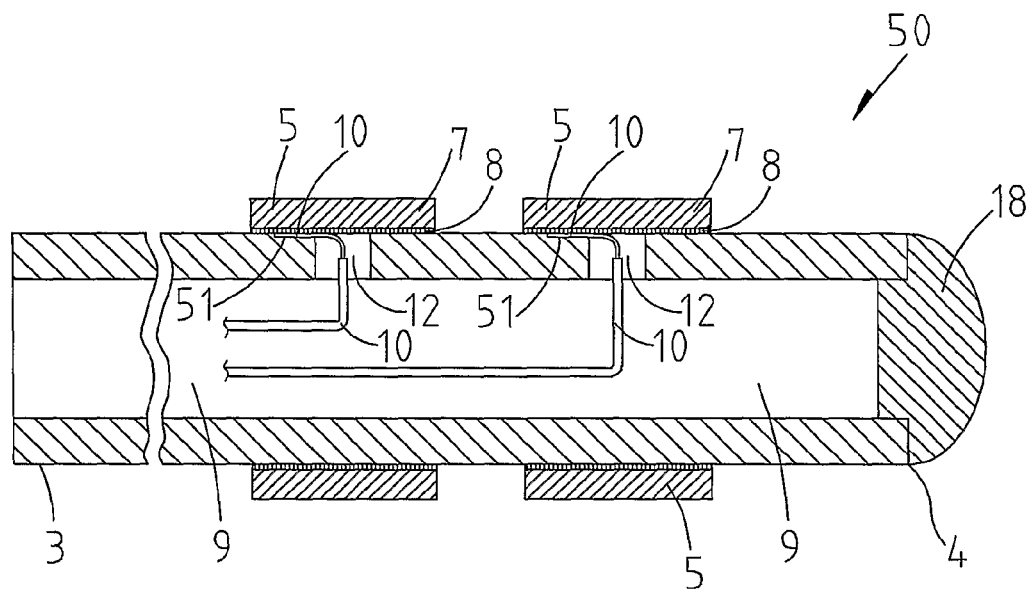
Fig. 5
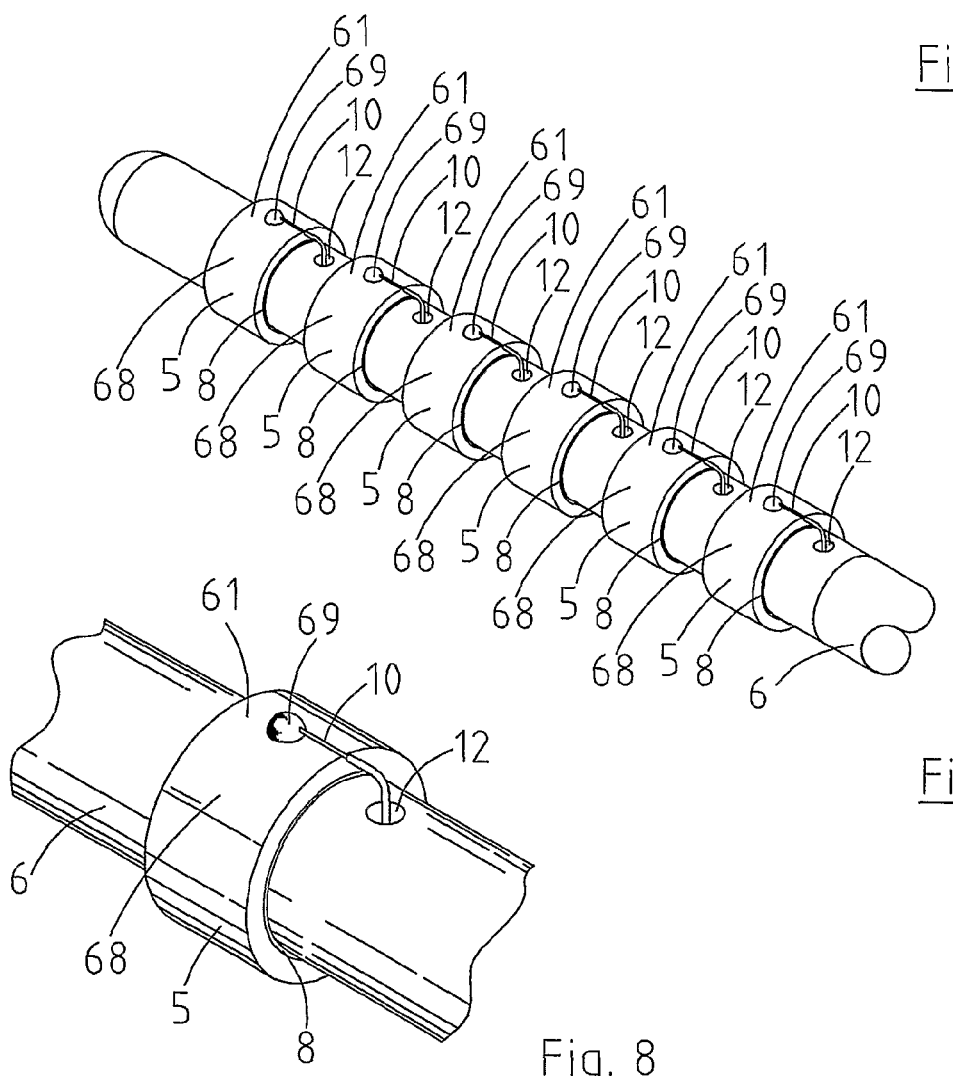
Fig. 7
Fig. 8

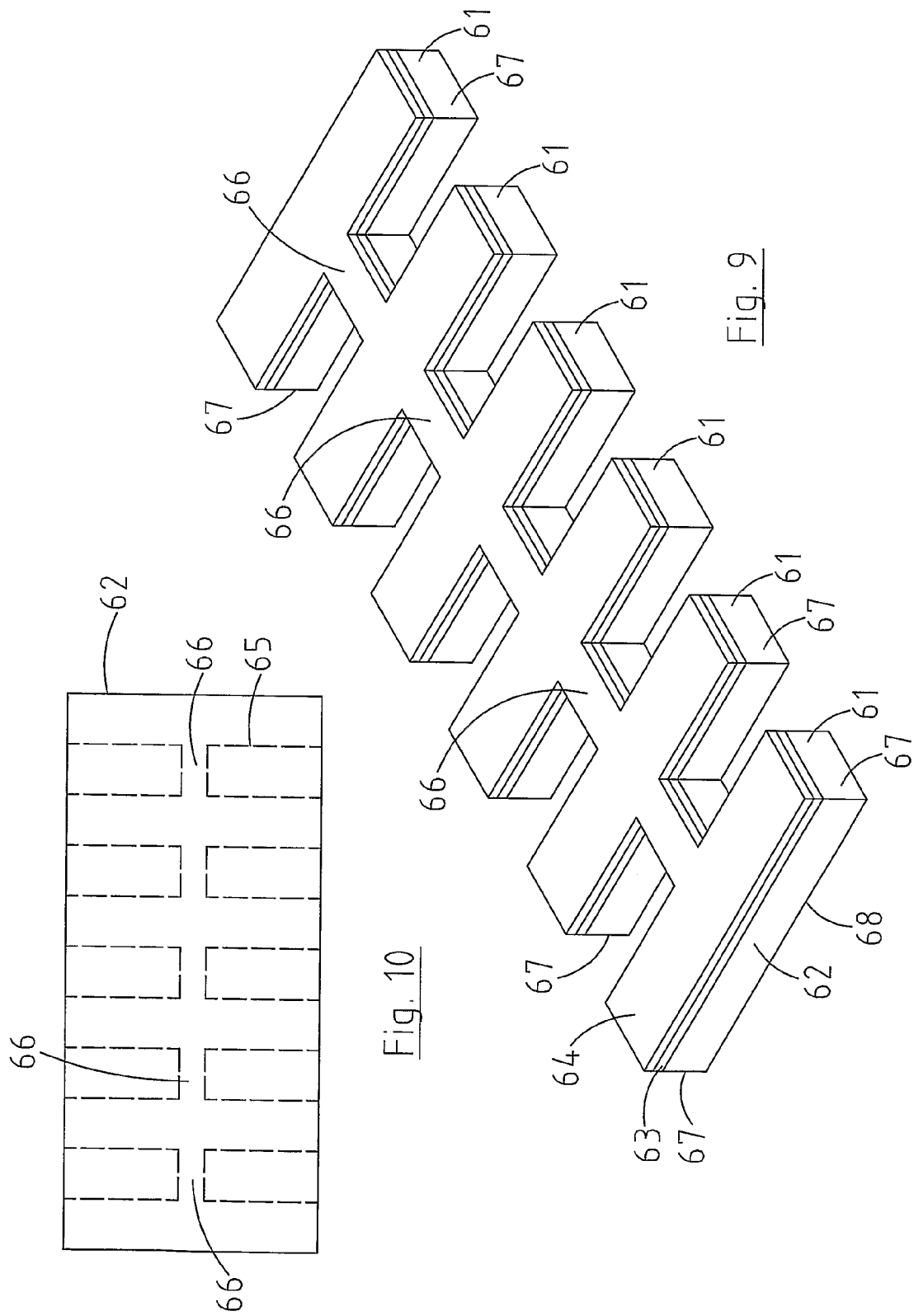

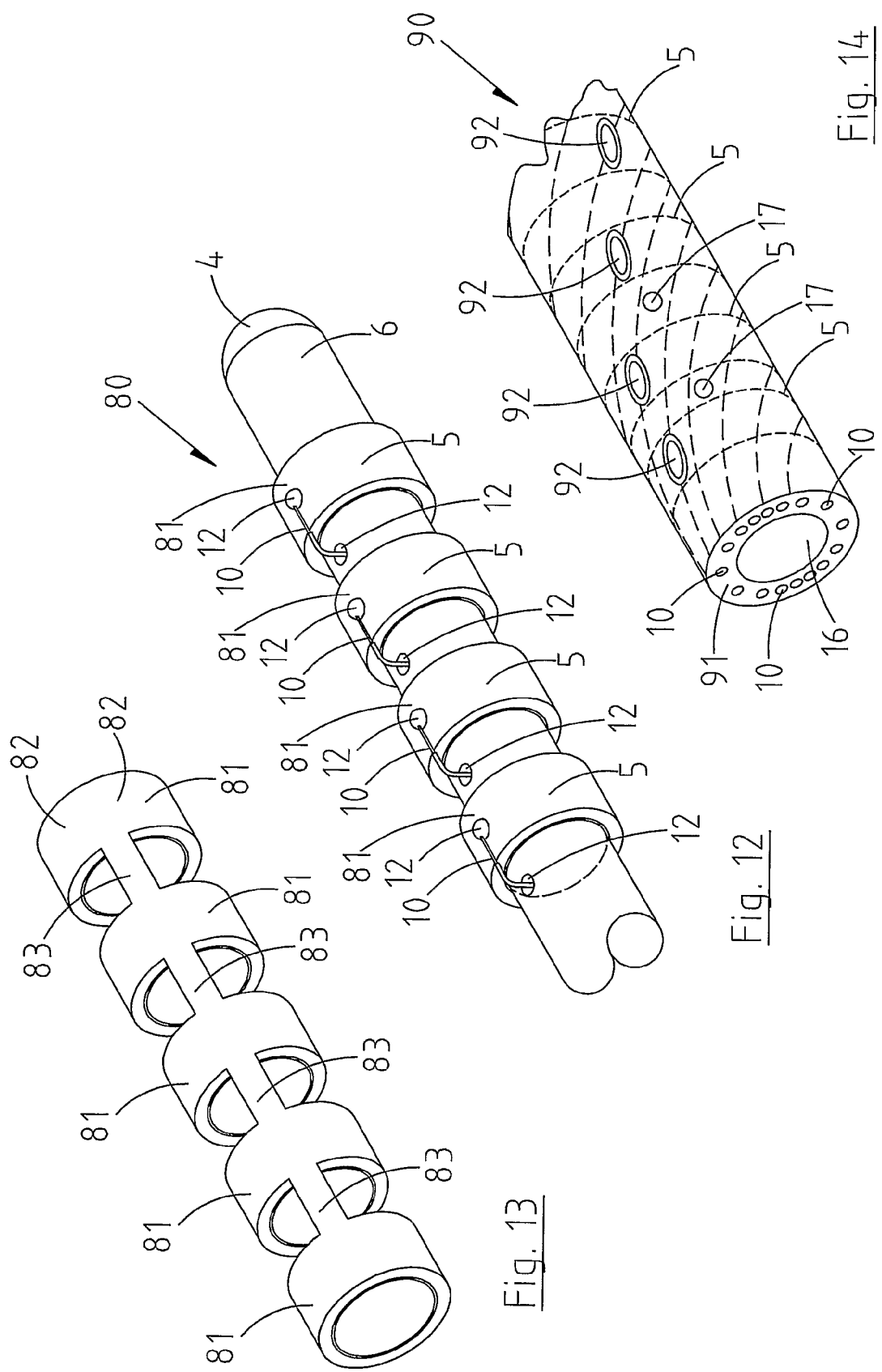

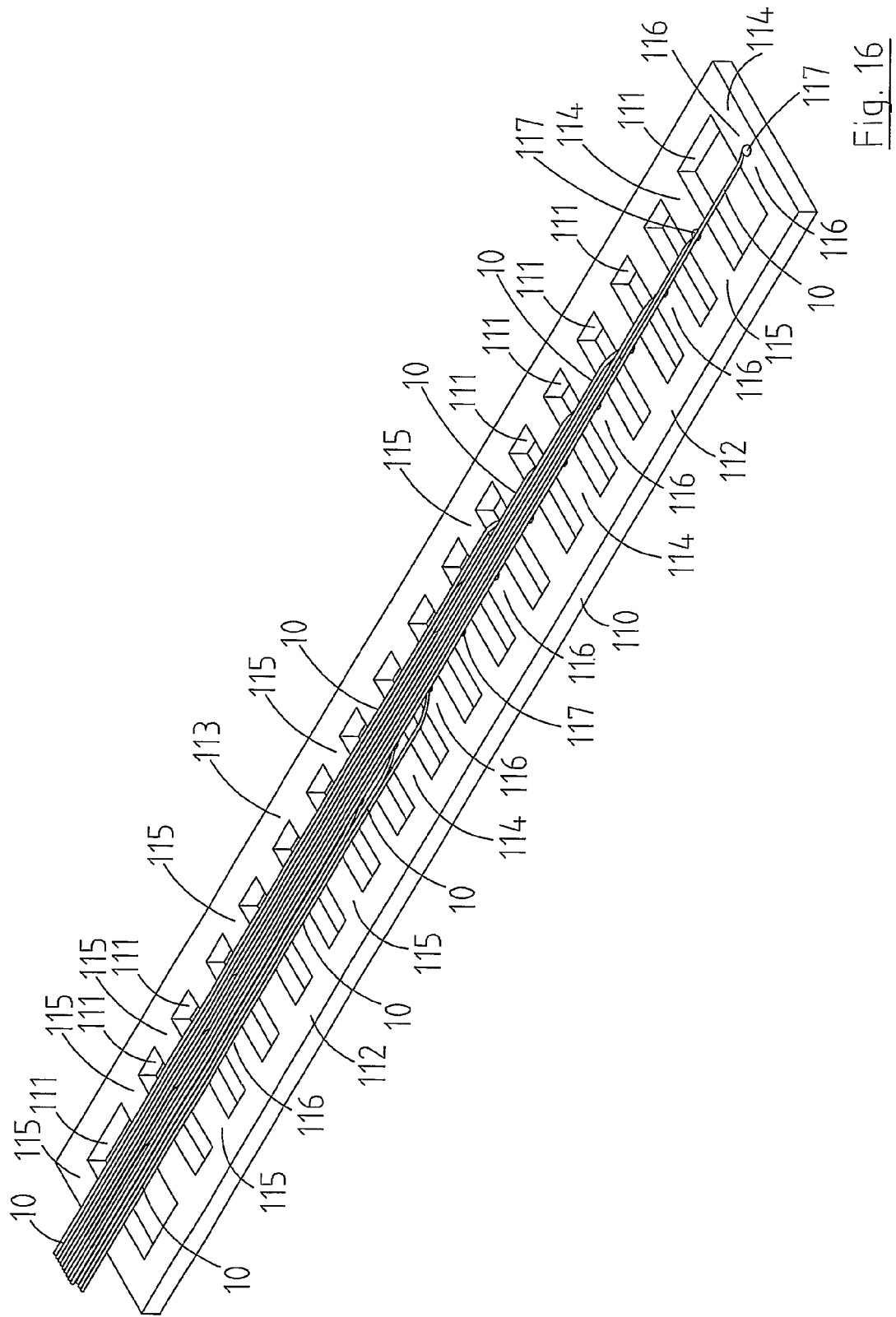

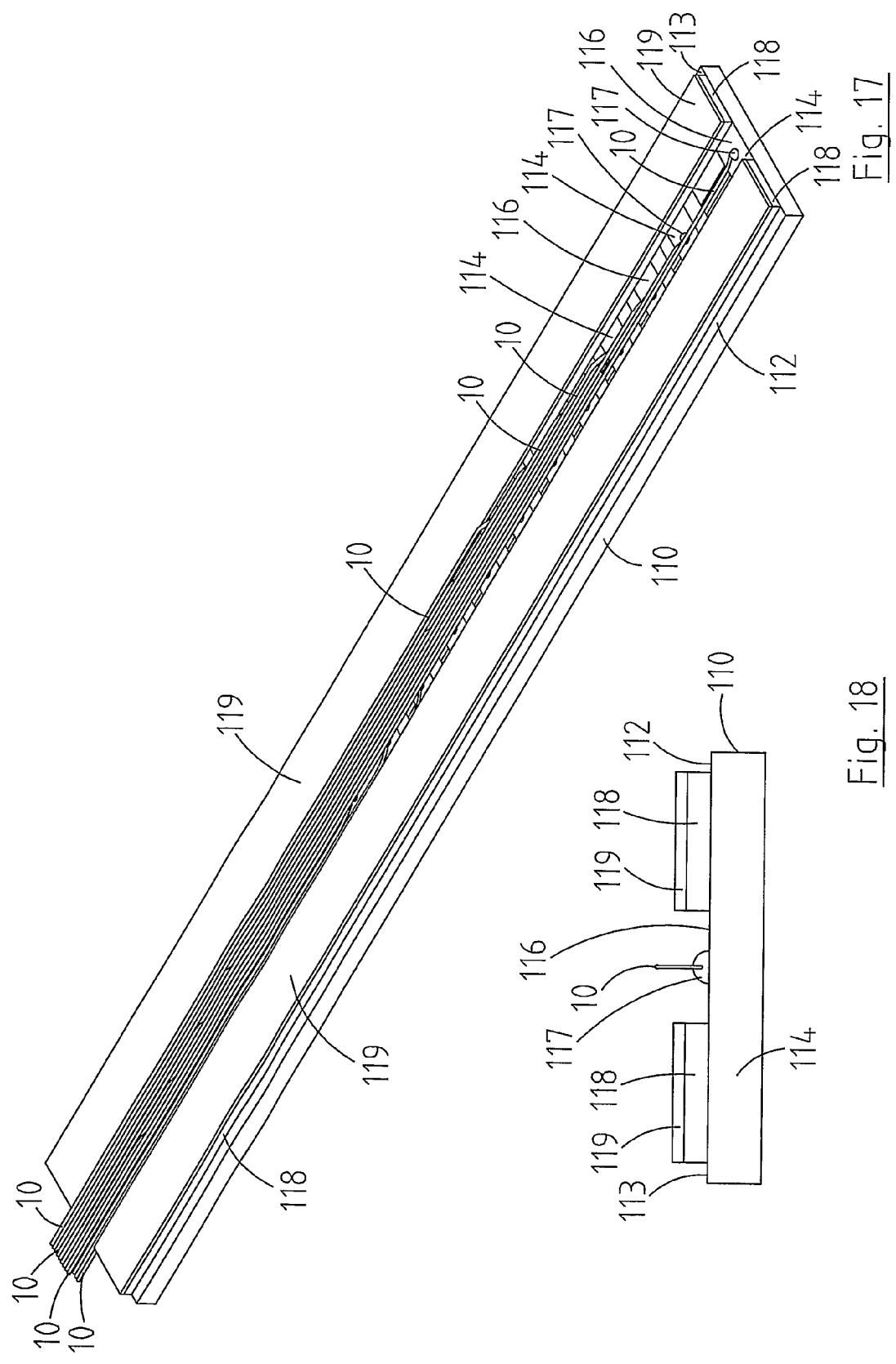

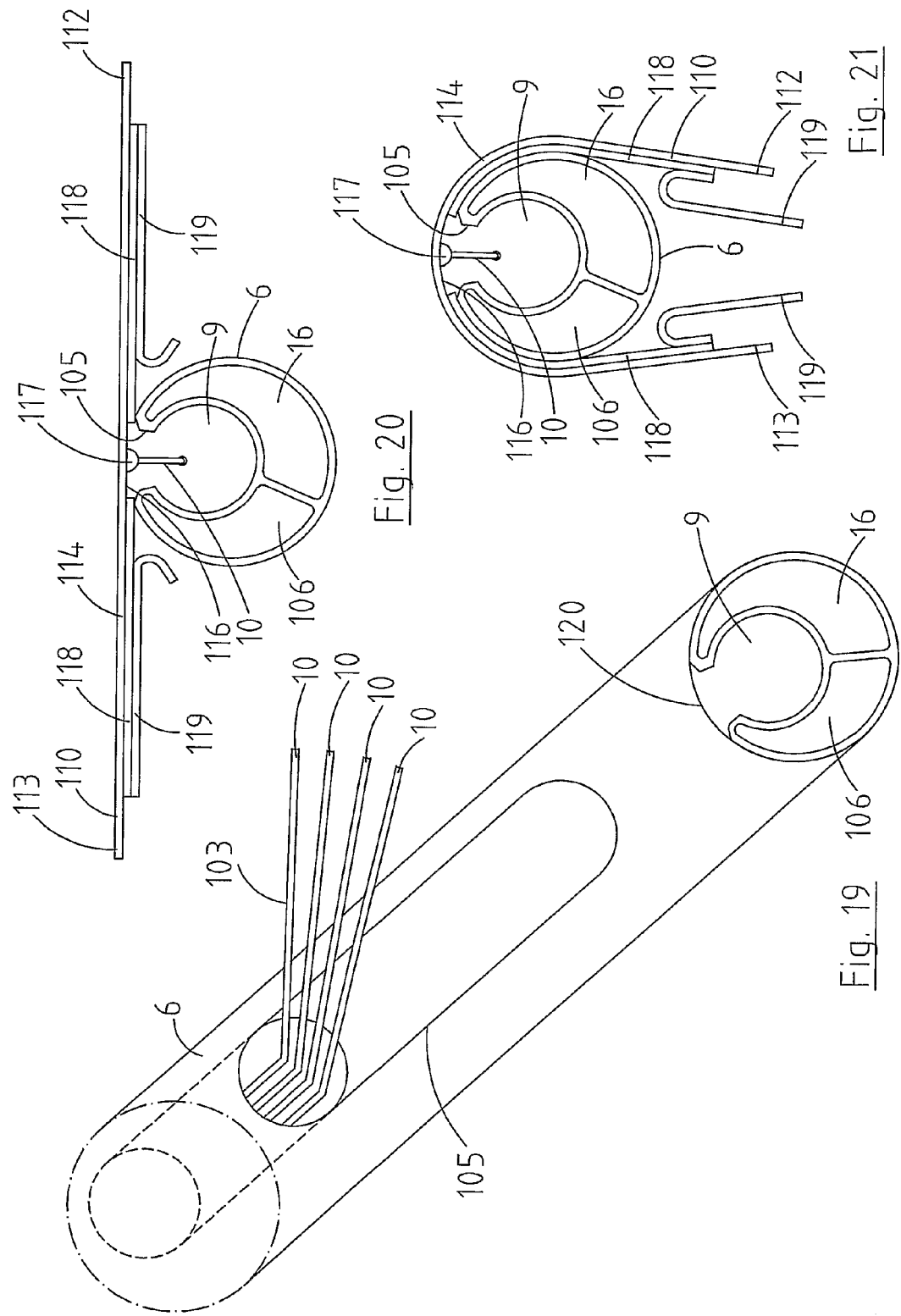

CATHETER AND A METHOD FOR PRODUCING A CATHETER

The present invention relates to a catheter and to a method for producing a catheter, and in particular, though not limited to a catheter and a method for producing a catheter of the type comprising a plurality of mutually electrically insulated axially spaced apart electrodes located towards a distal end of the catheter, and the catheter may or may not comprise an expandable member located adjacent the distal end thereof.

Such catheters are used in many medical and surgical procedures. Whether the catheter is provided with an expandable element or otherwise, such catheters are commonly used to perform a physical measurement, for example, to determine the volume of a vessel within which the catheter is located, to determine the compliance of a sphincter or other such organ by the use of pressure measurement or dimensional measurements, to ablate tissue and the like from, for example, a lumen such as an oesophagus, which may be occluded or partly occluded by cancerous growth or pre-cancerous growth of the tissue, to open an occlusion formed in a lumen, by, for example, a cancerous growth of tissue or a pre-cancerous growth thereof. Such catheters are disclosed, for example, in PCT Published Patent Application Specification No. WO 2006/090351, and U.S. Pat. Nos. 5,069,215, 6,032,061, 6,440,488 and 6,882,879.

U.S. Pat. No. 5,069,215 of Jadvar, et al discloses a catheter which is provided with a single use disposable oesophageal electrode structure located at a distal end thereof. The electrode structure comprises a planar sheet body member which carries a plurality of spaced apart electrically conductive electrode members, and a plurality of conducting members are coupled to the body member, and each conducting member is in turn coupled to a corresponding one of the respective electrodes. The conducting members extend from the electrode structure along the outer surface of the catheter to the distal end thereof, and free ends of the conducting members terminate in an electrical connector for connecting the electrodes to external electronic control and analysing apparatus. A layer of adhesive is provided on the sheet body member for releasably securing the sheet body member, and in turn the electrodes to the catheter at the distal end thereof. The electrode structure of the oesophageal catheter is provided to be disposable, and after use is removed from the distal end of the catheter and replaced by a new electrode structure.

U.S. Pat. No. 6,032,061 of Kobelish discloses an electrode catheter comprising a plurality of spaced apart ring electrodes located at the distal end thereof. A plurality of electrically conductive bands are printed onto the catheter adjacent the locations to which the ring electrodes are to be located. Electrically conductive wires extending through a lumen in the catheter extend through radial openings in the catheter, and skived ends of the wires are folded to lie along the printed electrically conductive bands. The ring electrodes are then slid over the electrically conductive bands to engage the skived ends of the wires between the printed electrically conductive bands and the corresponding ring electrodes for providing electrical continuity between the wires and the electrodes.

U.S. Pat. No. 6,440,488 of Griffin, et al discloses an electrode catheter which comprises a plurality of spaced apart electrodes located at a distal end thereof. Electrically conductive wires extend through the catheter from the proximal end thereof and extend through spaced apart radial openings in the catheter towards the distal end thereof. The portions of the wires extending through the radial openings are wrapped around the outer surface of the catheter to form the electrodes.

U.S. Pat. No. 6,882,879 of Rock discloses an electrode catheter comprising a plurality of spaced apart electrodes located towards a distal end thereof. A plurality of electrically conductive wires extend through the catheter from the electrodes to the proximal end thereof. The electrodes are located between spacers which form part of the catheter.

PCT Specification No. WO 2006/090351 discloses an electrode catheter having an inflatable balloon located at a distal end thereof with the catheter extending through the balloon. A plurality of spaced apart electrodes are located on the catheter within the balloon for determining the volume to which the balloon is inflated, and the transverse cross-sectional area thereof at predefined locations.

All the above electrode catheters suffer from various disadvantages. The electrode catheter disclosed in U.S. Pat. No. 6,882,879 is a particularly complex structure, and includes many components, all of which have to be assembled together. Thus, the manufacture of the electrode catheter of U.S. Pat. No. 6,882,879 is a relatively complex and time consuming task. The electrode catheter disclosed in U.S. Pat. No. 6,440,488 is also a relatively difficult and complex catheter to assemble, and furthermore, there is a danger of the free end of the wires which are wrapped around the outer surface of the catheter extending radially from the catheter with the potential to cause injury to a subject. The electrode catheter disclosed in U.S. Pat. No. 6,032,061 is also a relatively complex structure to assemble, and the assembly thereof is a relatively time consuming task. Additionally, by virtue of the fact that the ring electrodes are located on the surface of the catheter, the ring electrodes sit significantly proud of the catheter, and can result in discomfort to a subject. The electrode catheter of U.S. Pat. No. 5,069,215 suffers from the disadvantage that the electrically conductive members which electrically connect the electrodes to external control and analysing apparatus are located externally of the catheter, and thus, can result in discomfort to the subject. There is also a danger of the electrically conductive members becoming detached from the catheter with serious consequences. The catheter disclosed in PCT Specification No. WO 2006/090351 is also a relatively complex device and its manufacture is a relatively time consuming process.

There is therefore a need for a catheter and a method for producing a catheter which addresses at least some of the problems of known catheters.

The present invention is directed towards a catheter and a method for producing a catheter.

According to the invention there is provided a method for producing a catheter with at least one electrode thereon, the method comprising forming each electrode from an electrically conductive element, and bonding each electrically conductive element to the catheter to form the electrode thereon.

Preferably, the electrically conductive elements are bonded to the catheter by progressively wrapping the electrically conductive elements around the catheter. Advantageously, each electrically conductive element is bonded to the catheter by an adhesive. Preferably, each electrically conductive element is at least partially coated with an adhesive.

In one embodiment of the invention each electrically conductive element is at least partially coated with a self-adhesive coating.

In another embodiment of the invention the adhesive is provided by a double-sided adhesive tape. Preferably, the double-sided adhesive tape is bonded to the corresponding electrode prior to bonding to the catheter.

In one embodiment of the invention each electrically conductive element is of an electrically conductive foil material.

Preferably, a plurality of electrically conductive elements are formed from a single sheet of the electrically conductive foil material to produce corresponding electrodes. Advantageously, the foil material is of thickness up to 200 microns. Ideally, the foil material is of thickness in the range of 35 microns to 50 microns.

Preferably, the electrically conductive elements are formed from the single sheet of electrically conductive foil material prior to being bonded to the catheter.

Advantageously, adjacent ones of the electrically conductive elements are joined by respective connecting portions of the sheet of electrically conductive foil material. Preferably, the connecting portions extend between the respective adjacent ones of the electrically conductive elements intermediate the ends thereof. Advantageously, the connecting portions form an elongated connecting portion, and the electrically conductive elements extend transversely from the elongated connecting portion at spaced apart intervals therefrom.

Ideally, a pair of spaced apart elongated connecting portions are provided and the electrically conductive elements extend transversely between the elongated connecting portions.

In one embodiment of the invention each electrically conductive element is severed from at least one of the connecting portions connecting the electrically conductive element to an adjacent one of the electrically conductive elements subsequent to the electrically conductive elements being bonded to the catheter. Alternatively, each electrically conductive element is severed from at least one of the connecting portions connecting the electrically conductive element to an adjacent one of the electrically conductive elements prior to the electrically conductive element being bonded to the catheter.

In one embodiment of the invention each electrically conductive element is electrically coupled to a corresponding electrically conductive wire.

In one embodiment of the invention each electrically conductive element is coupled to the corresponding electrically conductive wire prior to the electrically conductive element being bonded to the catheter. Alternatively, each electrically conductive element is coupled to the corresponding electrically conductive wire subsequent to the electrically conductive element being bonded to the catheter.

Preferably, each electrically conductive wire is electrically coupled to the corresponding electrically conductive elements by one of soldering, welding, induction welding, ultrasonic welding and bonding by an electrically conductive adhesive. Advantageously, the electrically conductive wires are mutually insulated from each other.

Advantageously, each electrically conductive wire is coupled to the corresponding electrically conductive element at a location intermediate the ends of the electrically conductive element.

Ideally, the location at which each electrically conductive wire is coupled to the corresponding electrically conductive element is spaced apart from the respective ends thereof.

Preferably, each electrically conductive element is bonded to the catheter intermediate the location at which the corresponding electrically conductive wire is coupled thereto and at least one end of the electrically conductive element.

Ideally, each electrically conductive element is bonded to the catheter intermediate the location at which the corresponding electrically conductive wire is coupled thereto and the respective opposite ends of the electrically conductive element.

In one embodiment of the invention a plurality of the spaced apart electrically conductive elements are bonded to the catheter by at least one elongated piece of double-sided adhesive tape. Preferably, the at least one elongated piece of double-sided adhesive tape is located on the electrically conductive elements to at least one side of the locations at which the corresponding electrically conductive wires are coupled thereto. Advantageously, two elongated pieces of the double-sided adhesive tape are located on the electrically conductive elements on respective opposite sides of the locations at which the corresponding electrically conductive wires are coupled thereto.

Ideally, the respective electrically conductive elements extend transversely relative to each elongated piece of double-sided adhesive tape.

In one embodiment of the invention each elongated piece of double-sided adhesive tape is bonded to the catheter prior to being bonded to the electrically conductive elements. Alternatively, each elongated piece of double sided adhesive tape is bonded to the electrically conductive elements prior to being bonded to the catheter.

Preferably, a releasable protective sheet is provided over the adhesive surface of the double-sided adhesive tape to be bonded to the catheter. Advantageously, the releasable protective sheet is progressively removed from each elongated piece of double-sided adhesive tape as the double-sided adhesive tape is being bonded to the catheter.

Ideally, the electrically conductive elements are progressively bonded to the catheter by progressively wrapping the electrically conductive elements around the catheter from the respective locations at which the electrically conductive wires are coupled to the corresponding electrically conductive elements.

In another embodiment of the invention an axial communicating bore is formed in the catheter extending from a proximal end thereof to a location adjacent the at least one electrode for accommodating at least a corresponding one of the electrically conductive wires to the proximal end of the catheter, and at least one radial communicating opening is formed extending through the catheter adjacent the at least one electrode for accommodating at least the corresponding one of the electrically conductive wires from the corresponding one of the electrically conductive elements into the axial communicating bore.

Preferably, the at least one radial communicating opening extending through the catheter accommodates a plurality of the electrically conductive wires from respective corresponding ones of the electrically conductive elements into the axial communicating bore. Advantageously, the radial communicating opening is formed by an elongated slot in the catheter. Ideally, the elongated slot forming the radial communicating opening extends substantially longitudinally along the catheter adjacent the electrically conductive elements from which the corresponding electrically conductive wires are to be accommodated.

Preferably, the electrically conductive wires are passed into the axial communicating bore through the at least one first radial communicating opening prior to bonding of the electrically conductive elements to the catheter. Advantageously, each electrically conductive wire is electrically coupled to the corresponding electrically conductive element on a surface of the electrically conductive element which is adjacent the catheter when the electrically conductive element is bonded to the catheter.

In one embodiment of the invention each electrically conductive wire is electrically coupled to the corresponding one of the electrically conductive elements prior to the electrically conductive wire being entered into the axial communicating bore. Alternatively, each electrically conductive wire is electrically coupled to the corresponding one of the electrically conductive elements subsequent to the electrically conductive wire being entered into the axial communicating bore.

Preferably, a free end of each electrically conductive wire is trapped between the corresponding one of the electrically conductive elements and the catheter.

In another embodiment of the invention each electrically conductive wire is electrically coupled to the corresponding one of the electrically conductive elements by the adhesive bonding the electrically conductive element to the catheter.

In a further embodiment of the invention each electrically conductive wire is electrically coupled to the surface of the corresponding electrically conductive element remote from the catheter subsequent to the electrically conductive element being bonded to the catheter.

In another embodiment of the invention a wire accommodating opening extends through each electrically conductive element for accommodating a corresponding one of the electrically conductive wires therethrough, and the corresponding electrically conductive wire is electrically coupled to a surface of the electrically conductive element which is remote from the catheter when the electrically conductive element is bonded to the catheter.

Preferably, an insulating material on each electrically conductive wire is removed adjacent the corresponding distal end thereof for facilitating electrical coupling of the electrically conductive wire to the corresponding one of the electrically conductive elements.

In one embodiment of the invention each electrically conductive wire is electrically coupled to the corresponding one of the electrically conductive elements by an electrically conductive adhesive.

In another embodiment of the invention the electrically conductive wires are integrally formed with the catheter. Preferably, the electrically conductive wires are integrally formed in a wall of the catheter. Advantageously, the electrically conductive wires are helically wound around and within the catheter wall. Ideally, the electrically conductive wires are integrally formed in and helically wound around the catheter with a relatively long pitch. Preferably, the electrically conductive wires are one of integrally moulded and extruded with the catheter.

In one embodiment of the invention each electrically conductive element is of length sufficient to form the corresponding electrode as a band electrode extending at least partly around the catheter. Preferably, each electrically conductive element is of length sufficient to form the corresponding electrode as a band electrode extending completely around the catheter.

In another embodiment of the invention each electrically conductive element is of length sufficient to form the corresponding electrode as a band electrode extending completely around the catheter with one end of the electrically conductive element overlapping the opposite end thereof.

Preferably, the electrically conductive elements when bonded to the catheter are mutually electrically insulated from each other.

In one embodiment of the invention the adhesive with which each electrically conductive element is bonded to the catheter is an electrically conductive adhesive. Alternatively, the adhesive with which each electrically conductive element is bonded to the catheter is an electrically non-conductive adhesive.

Preferably, the adhesive with which each electrically conductive element is bonded to the catheter is one of a conductive adhesive, a pressure sensitive adhesive and a temperature sensitive adhesive.

In an alternative embodiment of the invention each electrically conductive element is of a semi-rigid electrically conductive material. Preferably, each electrically conductive element is secured to the catheter by crimping of the electrically conductive element to the catheter.

In one embodiment of the invention an axial medium accommodating bore is formed in the catheter extending axially from the proximal end thereof for accommodating a medium with fluid-like characteristics from the proximal end of the catheter towards the distal end thereof. Preferably, at least one radial medium accommodating bore is formed in the catheter extending radially through the catheter from the axial medium accommodating bore and communicates therewith for accommodating the medium with fluid-like characteristics into and out of the axial medium accommodating bore.

The invention also provides a catheter extending between a proximal end and a distal end and comprising at least one electrically conductive electrode located on an outer surface of the catheter, the at least one electrode being bonded to the outer surface of the catheter by the method as claimed in any preceding claim.

Further the invention provides a catheter extending between a proximal end and a distal end and comprising at least one electrically conductive electrode located on an outer surface of the catheter, the at least one electrode being bonded to the outer surface of the catheter.

Preferably, each electrode comprises an elongated electrically conductive element.

In one embodiment of the invention the adhesive is provided on each electrically conductive element intermediate the location at which the corresponding electrically conductive wire is coupled to the electrically conductive element and at least one of the respective opposite ends of the electrically conductive element.

Preferably, the adhesive is provided on each electrically conductive element intermediate the location at which the corresponding electrically conductive wire is coupled to the electrically conductive element and the respective opposite ends of the electrically conductive element.

Advantageously, a plurality of the electrically conductive elements are bonded to the catheter by at least one elongated piece of double-sided adhesive tape located between the electrically conductive elements and the catheter and intermediate the locations at which the electrically conductive wires are coupled to the electrically conductive elements and at least one of the respective opposite ends of the respective electrically conductive elements, the electrically conductive elements extending transversely of the double sided adhesive tape.

Ideally, two elongated pieces of double-sided adhesive tape are located between the electrically conductive elements and the catheter and intermediate the locations at which the electrically conductive wires are coupled to the electrically conductive elements and the respective opposite ends of the respective electrically conductive elements.

In one embodiment of the invention an axial communicating bore extends axially in the catheter from a proximal end thereof to a location adjacent the electrodes for accommodating the electrically conductive wires therethrough, and at least one radial communicating opening extends through the catheter from the axial communicating bore adjacent the electrodes for accommodating at least a corresponding one of the electrically conductive wires from the axial communicating bore to the corresponding one of the electrically conductive elements. Preferably, the at least one radial communicating opening accommodates a plurality of the electrically conductive wires to corresponding ones of the electrically conductive elements.

Advantageously, the radial communicating opening is formed by an elongated slot in the catheter. Preferably, the elongated slot forming the radial communicating opening extends substantially longitudinally along the catheter adjacent the electrically conductive elements to which the corresponding electrically conductive wires are to be accommodated.

In one embodiment of the invention the respective pieces of double-sided adhesive tape are located on respective opposite sides of the radial communicating opening and extend longitudinally along the catheter. Preferably, the double-sided adhesive tape is non-electrically conductive.

In one embodiment of the invention a wire accommodating opening extends through each electrically conductive element for accommodating a corresponding one of the electrically conductive wires therethrough, and the electrically conductive wire is electronically coupled to the electrically conductive element to the surface thereof remote from the catheter. Preferably, the wire accommodating opening extending through each electrode is aligned with a corresponding one of the radial communicating openings in the catheter.

In one embodiment of the invention the electrically conductive wires are mutually insulated from each other. Advantageously, each electrically conductive wire is coated with an electrically insulating coating.

In one embodiment of the invention each electrically conductive element forms the corresponding electrode as a band electrode extending at least partly around the catheter. Preferably, each electrically conductive element forms the corresponding electrode as a band electrode extending completely around the catheter. Advantageously, each electrically conductive element forms the corresponding electrode as a band electrode extending completely around the catheter with one end of the electrically conductive element overlapping the opposite end thereof.

Preferably, a plurality of electrically mutually insulated axially spaced apart electrodes are bonded to the outer surface of the catheter.

Advantageously, a double-sided adhesive tape is located between each electrically conductive element and the outer surface of the catheter for bonding the electrically conductive element to the catheter. Advantageously, the double-sided adhesive tape extends between adjacent ones of the electrically conductive elements.

In one embodiment of the invention each radial communicating opening extends through the catheter beneath the corresponding electrode.

Preferably, the electrodes are located on the catheter towards the distal end thereof.

In one embodiment of the invention an expandable element is located on the catheter adjacent the electrodes, the expandable element defining a hollow interior region, and the electrodes being located on the catheter within the hollow interior region defined by the expandable element. Preferably, the catheter extends through the hollow interior region of the expandable element. Advantageously, the expandable element is provided by an inflatable element. Ideally, the radial medium accommodating bore communicates the hollow interior region of the expandable element with the axial medium accommodating bore for accommodating an inflating medium to the expandable element for inflating thereof.

In another embodiment of the invention the expandable element comprises a balloon.

In another embodiment of the invention the expandable element when inflated defines a cylinder.

In a further embodiment of the invention the expandable element when inflated defines a central longitudinally extending axis substantially coinciding with a corresponding longitudinally extending axis of the catheter.

In a still further embodiment of the invention the expandable element is coated with a low friction coating. Preferably, the catheter is coated with a low friction coating.

In one embodiment of the invention the catheter is adapted for use in determining the transverse cross-sectional area of a lumen within which the portion of the catheter comprising the electrodes is located.

In another embodiment of the invention the catheter is adapted for use in determining the transverse cross-sectional area of a hollow organ, vessel or the like within which the portion of the catheter comprising the electrodes is located.

In a further embodiment of the invention the catheter is adapted for use in determining the volume of a lumen within which the portion of the catheter comprising the electrodes is located.

In a still further embodiment of the invention the catheter is adapted for use in determining the volume of a hollow organ, vessel or the like within which the portion of the catheter comprising the electrodes is located.

In another embodiment of the invention the catheter is adapted for use in a procedure for ablating a stricture in a lumen.

In a further embodiment of the invention the catheter is adapted for use in a procedure for ablating tissue in a hollow organ or vessel.

Preferably, each electrode extends transversely across the radial communicating opening in the catheter.

The advantages of the invention are many. The method for producing the catheter provides a relatively inexpensive and simple procedure for producing a catheter, which requires little manufacturing time. By bonding the electrodes to the catheter, a simple, inexpensive and relatively quick method is provided for producing the catheter. By forming the electrodes from a sheet of foil material whereby prior to being secured to the catheter the electrodes are retained spaced apart by connecting portions of the foil extending between the electrodes, or by an elongated connecting portion from which the electrodes extend in spaced apart relationship, the electrodes can be attached to the catheter in a single operation. This significantly reduces the time required for assembling the electrodes to the catheter, and furthermore, by virtue of the fact that the electrodes are formed by the electrically conductive elements which are retained spaced apart by the connecting portions or by a single elongated connecting portion, the electrodes are accurately spaced apart from each other when secured to the catheter. Additionally, by securing the electrodes to the catheter by double-sided adhesive tape, a particularly efficient method for assembling and securing the electrodes to the catheter is provided.

Additionally, by providing the electrodes of foil material, and in particular, foil material of thickness not greater than 200 microns, and preferably, of thickness in the order of 35 microns to 50 microns, a particularly advantageous catheter is provided. By providing the electrodes of such foil material, the catheter provides a substantially constant longitudinal cross-sectional profile along its length, including along its length on which the electrodes are provided. The electrodes being of such relatively thin material add virtually no additional thickness to the catheter, and therefore, the catheter is effectively free of steps or bumps, which could otherwise snag on equipment through which the catheter is being passed, or on a side wall of a lumen or vessel through which the catheter is being urged. Furthermore, by providing the electrodes of such relatively thin foil material, the electrodes when bonded to the catheter are relatively flexible, and thus, flex with flexing of the catheter, and do not inhibit flexing of the catheter. Indeed, by providing the electrodes of such relatively thin foil material, the catheters can be produced of relatively small cross-section, typically, down to 2 mm in diameter, and typically, of diameter in the range of 2 mm to 7 mm. Furthermore, by producing the catheter with the method according to the invention whereby the electrodes are formed of electrically conductive elements which are joined by connecting portions, the method is particularly suitable for use with catheters of relatively small diameter in the range of 2 mm to 7 mm.

Ideally, the width of each electrode in the longitudinal direction of the catheter ranges from 1 mm to 5 mm. Additionally, by forming the electrodes from a single sheet of foil material whereby the electrodes are formed by the elongated electrically conductive elements which are joined by connecting portions or an elongated connecting portion, or two elongated connecting portions at respective opposite ends of the electrically conductive elements, the electrically conductive elements can be readily easily electrically coupled to the corresponding electrically conductive wires by any suitable electrical coupling, for example, soldering, welding or adhesive bonding.

By providing the radial communicating opening in the catheter as an elongated longitudinally extending slot for accommodating the electrically conductive wires from the catheters, the wires can be initially electrically coupled to the underside of the electrodes, namely, the surface of the electrodes which is adjacent the catheter prior to assembling the electrodes to the catheter, and the wires can be readily easily inserted through the elongated slot into the first axial communicating bore of the catheter and then urged through the first axial communicating bore to the proximal end thereof prior to securing the electrodes to the catheter.

Figure 2:
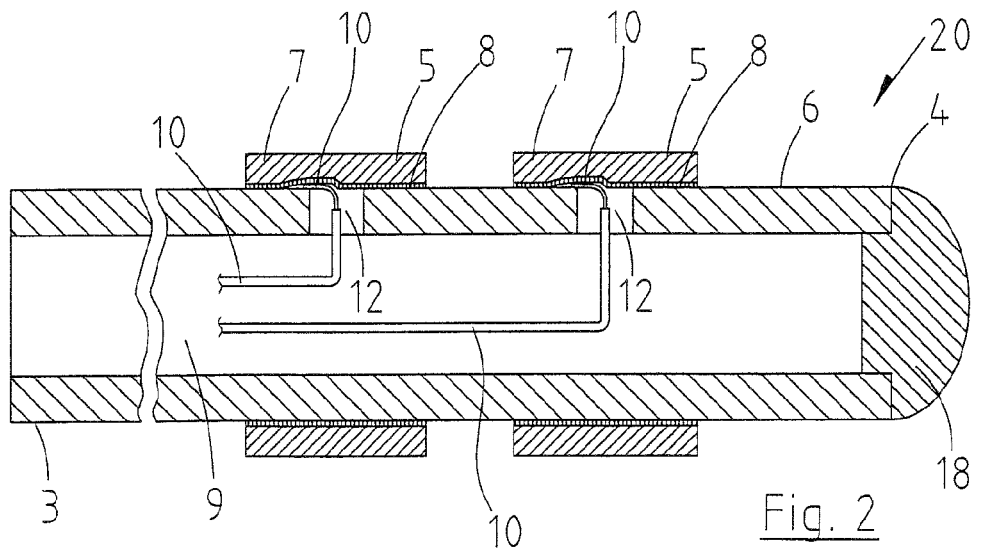
Figure 11:
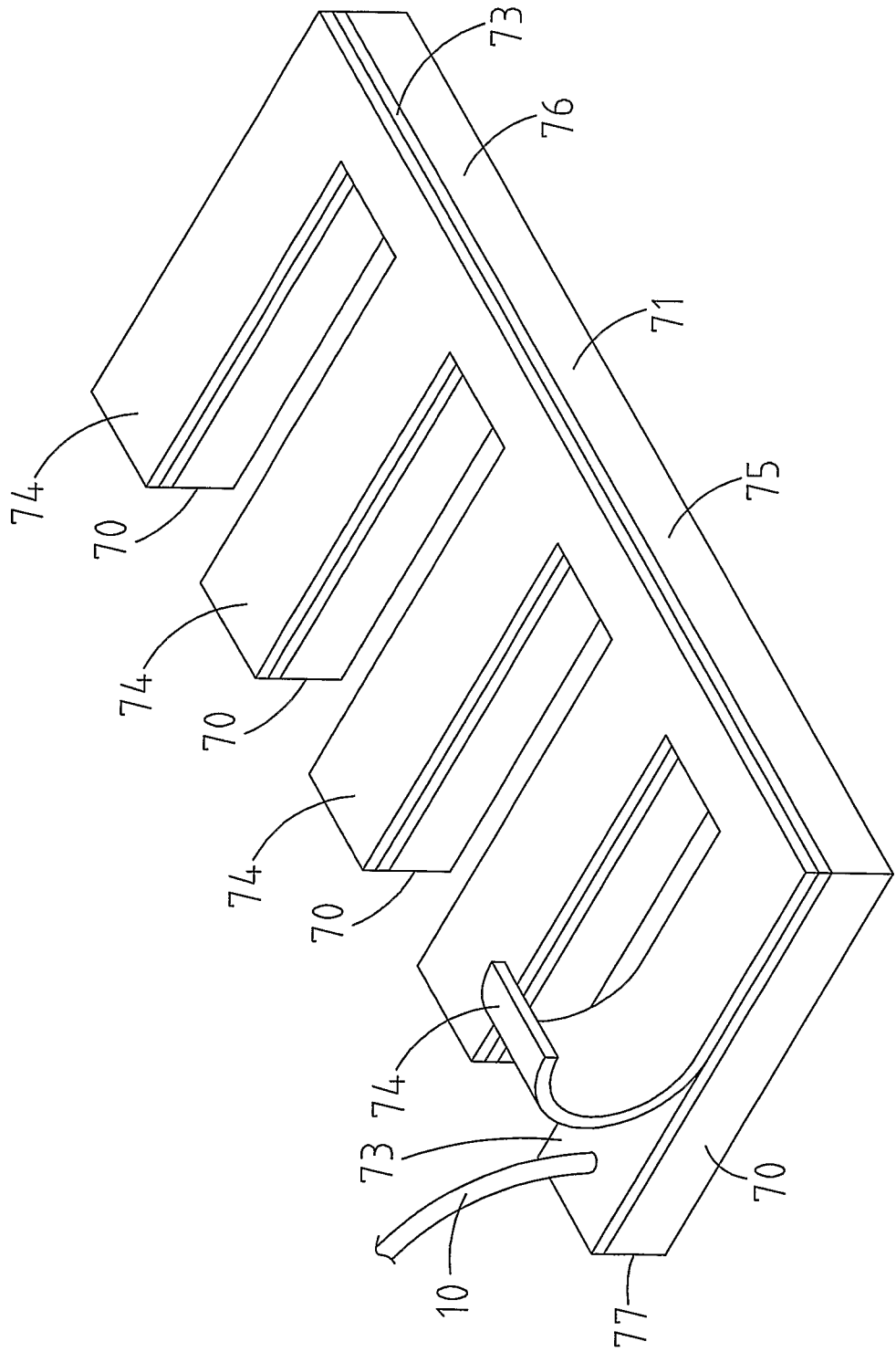
Figure 23:
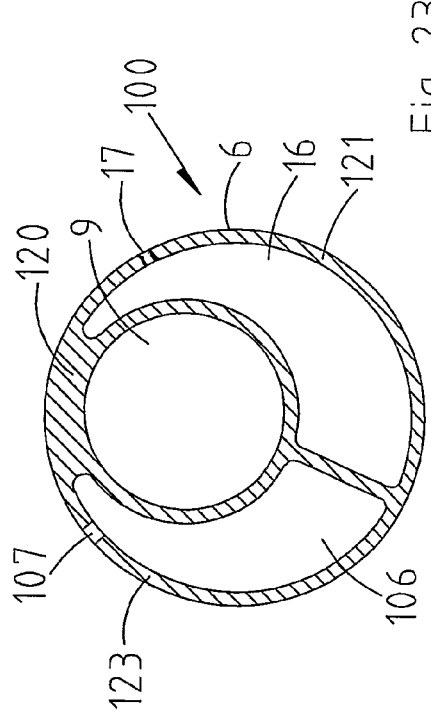
Figure 22:
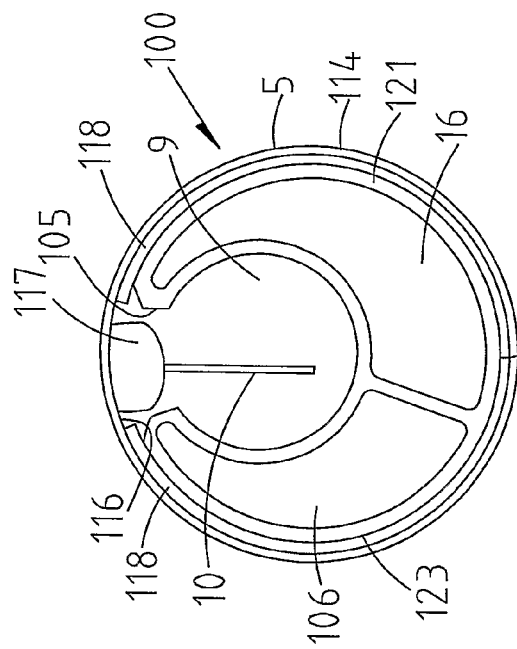
Figure 15:
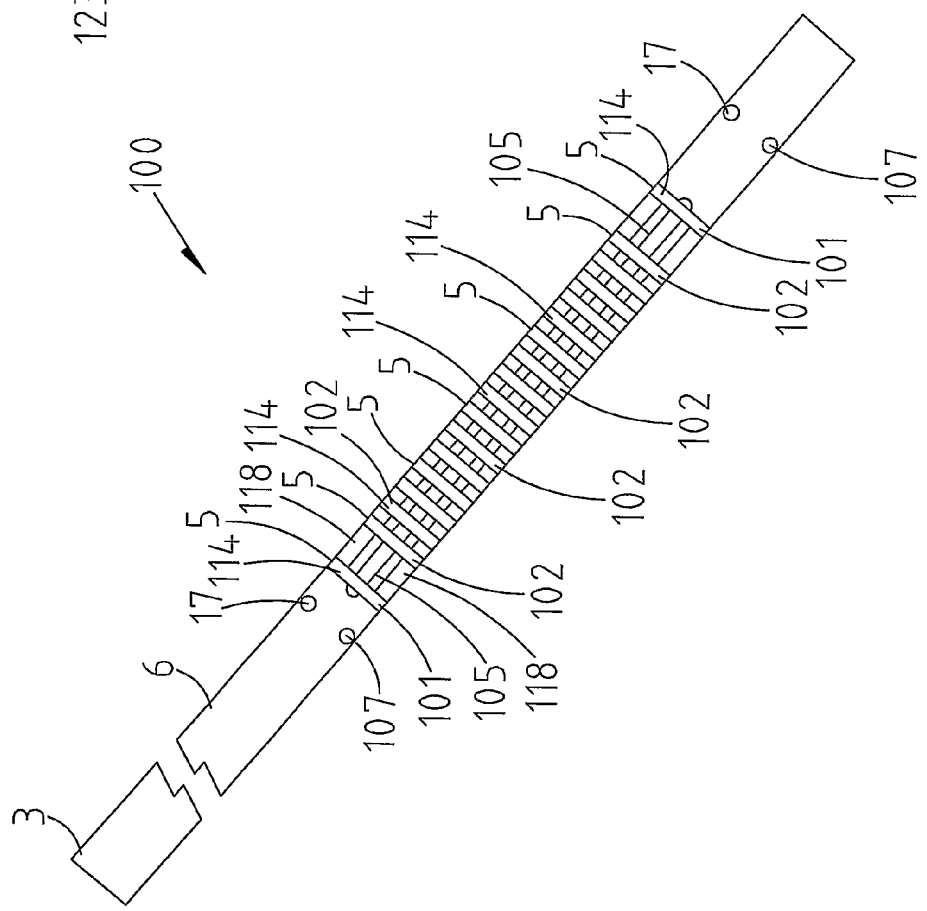
Figure 24:
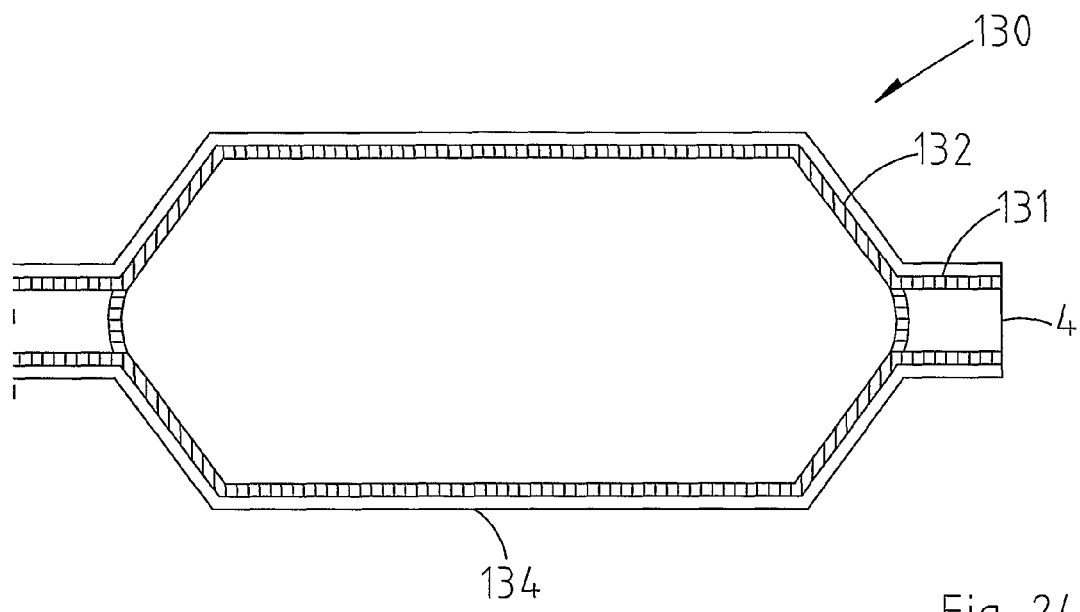
Figure 25:
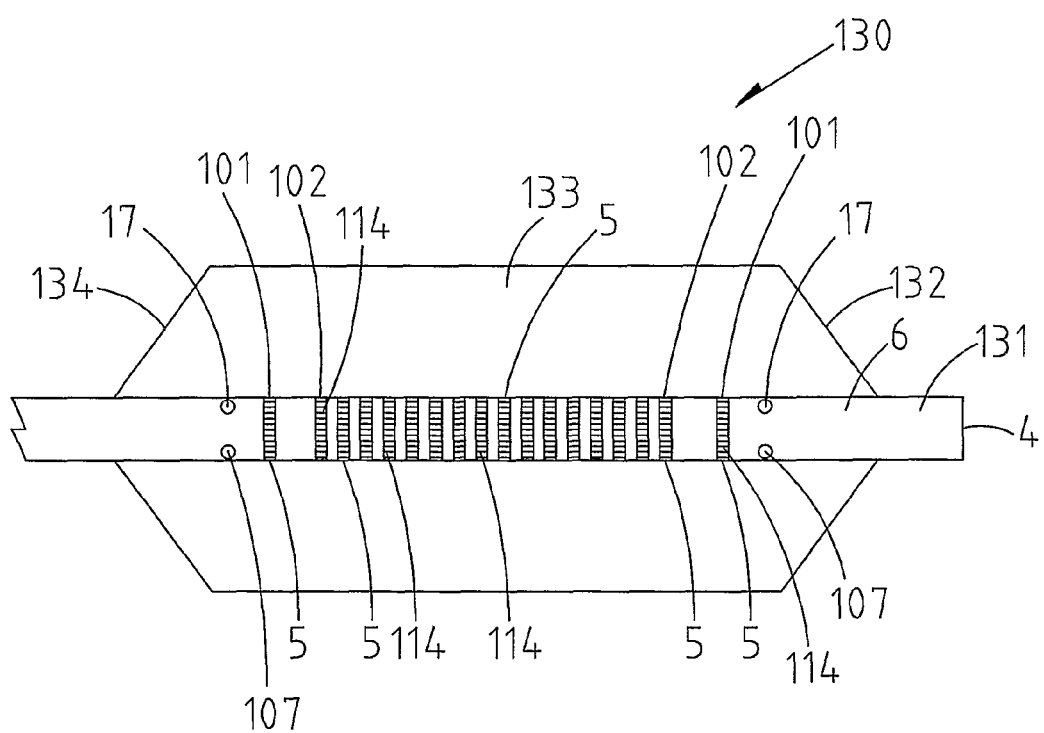

The invention will be more clearly understood from the following description of some preferred embodiments thereof, which are given by way of example only, with reference to the accompanying drawings, which are not to scale, and in which:

FIG. 1 is a transverse cross-sectional side elevational view of a portion of a catheter according to the invention, FIG. 2 is a view similar to FIG. 1 of a portion of a catheter according to another embodiment of the invention, FIG. 3 is a view similar to FIG. 1 of a portion of a catheter according to a further embodiment of the invention, FIG. 4 is a transverse cross-sectional side elevational view of a portion of a catheter according to another embodiment of the invention, FIG. 5 is a view similar to FIG. 1 of a portion of a catheter according to a still further embodiment of the invention, FIG. 6 is a transverse cross-sectional end elevational view of the catheter of FIG. 5, FIG. 7 is a perspective view of a distal end portion of a catheter according to another embodiment of the invention, FIG. 8 is an enlarged perspective view of a portion of the catheter of FIG. 7, FIG. 9 is a perspective developed view of another portion of the catheter of FIG. 7, FIG. 10 is a top plan view of the portion of FIG. 9 being formed, FIG. 11 is a perspective developed view of a portion of a catheter which may be used in connection with any of the catheters of FIGS. 1 to 10, FIG. 12 is a perspective view of a distal end portion of another catheter also according to the invention, FIG. 13 is a perspective view of a portion of the catheter of FIG. 12, FIG. 14 is a perspective view of a distal end portion of another catheter according to another embodiment of the invention, FIG. 15 is a side elevational view of a portion of a catheter according to a further embodiment of the invention, FIG. 16 is a perspective view of a portion of the catheter of FIG. 15, FIG. 17 is another perspective view of the portion of FIG. 16, FIG. 18 is an end elevational view of the portion of FIG. 17, FIG. 19 is a perspective view of another portion of the catheter of FIG. 15, FIG. 20 is a transverse cross-sectional end elevational view of the catheter of FIG. 15 being assembled, FIG. 21 is a transverse cross-sectional end elevational view similar to FIG. 20 of the catheter of FIG. 15 also being assembled, FIG. 22 is a transverse cross-sectional end elevational view of the catheter of FIG. 15, FIG. 23 is a transverse cross-sectional end elevational view of a portion of the catheter of FIG. 15, FIG. 24 is a side elevational view of a portion of a catheter according to a still further embodiment of the invention, and FIG. 25 is a transverse cross-sectional side elevational view of the portion of the catheter of FIG. 24.

Referring to the drawings and initially to FIG. 1, there is illustrated a catheter according to the invention, indicated generally by the reference numeral 1, which is produced by a method also according to the invention. The catheter 1 is of an extruded polymer material and extends from a proximal end 3 to a distal end 4, and comprises a plurality of axially spaced apart electrodes 5 located on an outer surface 6 of the catheter 1 adjacent the distal end 4. Although in FIG. 1 only two electrodes 5 are illustrated, many more electrodes similar to the two electrodes 5 illustrated are provided, and in this particular embodiment of the invention twenty electrodes are provided. The electrodes 5 may be provided for many uses, for example, for use in determining the cross-sectional area or volume of a lumen, a hollow organ, vessel or the like, into which the distal end 4 of the catheter 5 is inserted or for ablating cancerous or otherwise infected tissue in a hollow organ, for example, the oesophagus, or other such organ, vessel or the like. The use of catheters in determining transverse cross-sectional area and/or volume of a hollow organ or for ablating tissue will be well known to those skilled in the art.

Each electrode 5 in this embodiment of the invention is formed by an electrically conductive element, which in this case comprises an elongated strip of electrically conductive tape 7 having an adhesive backing 8 which bonds the electrically conductive tape 7 onto the outer surface 6 of the catheter 1. The electrically conductive tape 7 extends completely around the catheter 1 to form a band electrode, and preferably, is of thickness in the range of 35 microns to 50 microns. Any suitable electrically conductive tape may be used, however, in this embodiment of the invention the adhesive backed electrically conductive tape 7 is, for example, conductive Electromask Tape sold by Laird Technologies of St Louis, Mo., United States of America. The adhesive backing on the tape 7 is a contact adhesive, and may be electrically conductive or non-electrically conductive. In this embodiment of the invention the electrical conductivity or otherwise of the adhesive backing on the tape 6 is not important.

An axial communicating bore 9 extends axially through the catheter 1 from the proximal end 3 to the distal end 4 thereof for accommodating electrically conductive means, namely, a plurality of insulated electrically conductive wires 10 which are electrically coupled to the electrodes 5. One electrically conductive wire 10 is provided for each electrode 5. Radial communicating openings 12 extend radially through the catheter 1 from the axial communicating bore 9 for accommodating the wires 10 therethrough to the respective corresponding electrodes 5. Each wire 10 is electrically coupled to the tape 7 of the corresponding electrode 5 to an outer surface of the tape 7, namely, the surface of the tape 7 remote of the catheter 1 by an electrically conductive adhesive 14. Prior to coupling the wires 10 to the electrodes 5 by the adhesive 14, insulation is skived from the distal ends of the wires 10. The wires 10 extend from the electrodes 5 through the corresponding radial communicating openings 12, and in turn through the axial communicating bore 9 to the proximal end 3 thereof, and extend outwardly from the proximal end 3 for coupling to electronic control and analysing apparatus (not shown) of the type which will be well known to those skilled in the art. Alternatively, the distal ends of the wires 10 may be coupled to the electrodes 5 by soldering, welding, induction welding, ultrasonic welding or any other suitable electrical coupling means, and in the case of soldering and welding, the insulation on the wires 10 is sufficiently thin such that the insulation would melt during soldering or welding, thereby obviating the need to skive the ends of the wires 10.

An axial medium accommodating bore 16 extends axially through the catheter 1 from the proximal end 3 thereof to the distal end 4 for accommodating a fluid therethrough. A plurality of radial medium accommodating bores 17 extends through the catheter 1 adjacent the distal end 4 thereof and communicates with the axial medium accommodating bore 16 for accommodating fluid into or out of the axial medium accommodating bore 16. The catheter 1 terminates at its distal end in an epoxy plug 18 of hemispherical shape which seals the distal end of the axial communicating bore 9 and the axial medium accommodating bore 16. Alternatively, the distal tip of the catheter 1 may be melted to seal the distal ends of the bores 9 and 16. The axial and radial medium accommodating bores 16 and 17 may be used for delivering a fluid to a hollow organ into which the catheter 1 has been inserted, for example, an electrically conductive medium, such as an electrically conductive saline solution, which may be used for determining the cross-sectional area of the organ or the volume thereof, and additionally or alternatively the second axial and radial medium accommodating bores 16 and 17 may be used for withdrawing a fluid from the hollow organ, such as a sample of body fluid.

Depending on the use to which the catheter 1 is to be put, the catheter is inserted into a hollow organ or vessel of a subject. The organ or vessel may be any organ, for example, the oesophagus, the colon, intestine, urethra, an artery, vein, a cavity of the heart, the lung or the like. The wires 10 of the catheter 1 are coupled to the electronic control and analysing apparatus (not shown), and if appropriate, a fluid is delivered to the organ or removed therefrom through the second axial and radial bores 16 and 17.

To manufacture the catheter 1, the catheter 1 is extruded with the axial bores 9 and 16 extending therethrough. The radial openings 12 and the radial bores 17 are drilled into the respective axial bores 9 and 16, respectively. The electrically conductive tapes 7 are wrapped around the catheter 1 at appropriate axial spacings adjacent the bores 12, and bonded thereto by the adhesive backing 8. The wires 10 are passed into the axial communication bore 9 through the respective radial communicating openings 12 and urged along the axial communicating bore 9 until they exit the proximal end 3 of the bore 9. The distal ends of the wires 10 are skived and electrically coupled to the respective adjacent tapes 7 to the outer surface thereof by the electronically conductive adhesive 14. The distal ends 4 of the bores 9 and 16 are sealed by the epoxy plug 18.

Referring now to FIG. 2, there is illustrated a catheter 20 according to another embodiment of the invention. The catheter 20 is substantially similar to the catheter 1 and similar components are identified by the same reference numerals. The main difference between the catheter 20 and the catheter 1 is in the coupling of the wires 10 to the tapes 7 of the respective electrodes 5. In this embodiment of the invention the tapes 7 of the respective electrodes 5 extends around the catheter 1 over the radial communicating openings 12 and the skived ends of the wires 10 are entrapped between the corresponding tapes 7 and the catheter 1. In this case the adhesive backing 8 on the tapes 7 is an electrically conductive contact adhesive for electrically coupling the skived ends of the wires 10 to the tapes 7.

To assemble the catheter 20 according to this embodiment of the invention the wires 10 are passed through the radial communicating openings 12 into the axial communicating bore 9 and urged through to the proximal end 3. The ends of the wires 10 extending from the radial communicating openings 12 are skived and folded over to lie longitudinally along the outer surface 6 of the catheter 20. The adhesive backed tape 7 forming each electrode 5 is then wrapped around the catheter 1 over the corresponding radial communicating opening 12 with the skived end of the corresponding wire 10 entrapped between the tape 7 and the catheter 20 with the wire 10 electrically coupled to the tape 7 by the electrically conductive backing adhesive 8.

Although for convenience an axial medium accommodating bore and radial medium accommodating bores have not been illustrated in the catheter 20, such bores, if desired, may also be provided.

Otherwise, the catheter 20 is similar to the catheter 1.

Referring now to FIG. 3, there is illustrated a catheter 30 according to another embodiment of the invention. The catheter 30 is substantially similar to the catheter 1, and similar components are identified by the same reference numerals. The main difference between the catheter 30 and the catheter 1 is that the adhesive backed tape 7 of each electrode 5 is located over the corresponding radial communicating opening 12, and is provided with a wire accommodating opening 31 extending therethrough. The wire accommodating opening 31 of each electrode 5 is aligned with the corresponding radial communicating opening 12 for accommodating the corresponding wire 10 therethrough to an outer surface 32 of the tape 7. The skived ends of the wires 10 are folded over and electrically coupled to the outer surface 32 of the corresponding tape 7 by an electrically conductive adhesive 33, which typically closes the wire accommodating opening 31 of the corresponding tape 7. In this embodiment of the invention the electrically conductive tape 7 may be adhesive backed with an electrically conductive or a non-electrically conductive adhesive.

Although for convenience an axial medium accommodating bore and radial medium accommodating bores have not been illustrated in the catheter 30, such bores, if desired, may also be provided.

Otherwise, the catheter 30 is similar to the catheter 1.

Referring now to FIG. 4, there is illustrated a portion of a catheter 40 according to another embodiment of the invention. The catheter 40 is substantially similar to the catheter 1, and similar components are identified by the same reference numerals. The main difference between the catheter 40 and the catheter 1 is that instead of the wires 10 being electrically coupled to the adhesive backed tapes 7 of the corresponding electrodes on an outer surface of the tapes 7, the skived ends of the wires 10 corresponding to the respective electrodes 5 are entrapped between the tapes 7 and the catheter 1, in similar fashion as that of the catheter 20. The adhesive backing 8 of the tapes 7 is an electrically conductive contact adhesive, and the skived ends of the wires 10 are electrically coupled to the corresponding tapes 7 by the adhesive backing 8.

Although for convenience an axial medium accommodating bore and radial medium accommodating bores have not been illustrated in the catheter 40, such bores, if desired, may also be provided.

Otherwise the catheter 40 is similar to the catheter 1.

Referring now to FIGS. 5 and 6, there is illustrated a catheter according to another embodiment of the invention, indicated generally by the reference numeral 50. The catheter 50 is substantially similar to the catheter 1 and similar components are identified by the same reference numerals. The only difference between the catheter 50 and the catheter 1 is that the skived ends of the wires 10 are accommodated in longitudinally extending grooves 51 which extend longitudinally from the corresponding radial communicating opening 12. In fact, the construction of the catheter 50 is almost identical to the construction of the catheter 20 of FIG. 2, with the exception that the skived ends of the wires 10 are recessed into the longitudinal grooves 51. The depth of each groove 51 is substantially similar to, but just less than, the diameter of the transverse cross-section of the skived ends of the wires 10 so that when the skived ends of the wires 10 are located in the corresponding grooves 51, the skived ends of the wires 10 abut the adhesive backing 8 of the tapes 7 of the corresponding electrodes 5. In this embodiment of the invention the adhesive backing 8 of the tapes 7 of the electrodes 5 is an electrically conductive contact adhesive for maintaining electrical continuity between the wires 10 and the respective tapes 7 of the corresponding electrodes 5.

Although for convenience an axial medium accommodating bore and radial medium accommodating bores have not been illustrated in the catheter 50, such bores, if desired, may also be provided.

Referring now to FIGS. 7 to 10, there is illustrated a distal portion of a catheter according to another embodiment of the invention, indicated generally by the reference numeral 60. The catheter 60 is substantially similar to the catheter 1, and similar components are identified by the same reference numerals. The catheter 60 comprises a plurality of axially spaced apart electrodes 5 which extend completely circumferentially around the outer surface 6 of the catheter 60. Each electrode 5 comprises an electrically conductive element 61, and the electrically conductive elements 61 are formed from a single sheet 62 of electrically conductive metallic foil of thickness of the order of 35 microns to 50 microns having an adhesive backing 63.

A protective releasable sheet 64 protects the adhesive backing 63 of metallic foil sheet 62. In this embodiment of the invention the electrically conductive elements 61 extend circumferentially completely around the catheter 60 to form the electrodes 5 as band electrodes.

To form the electrically conductive elements 61, the sheet 62 of metallic foil is cut along the broken lines 65 illustrated in FIG. 10 to form the electrically conductive elements 61 and to form connecting portions 66 located between and connecting the electrically conductive members 61 in the appropriate spaced relationship. In this embodiment of the invention the electrically conductive elements 61 are to be equi-spaced apart from each other, and accordingly, the connecting portions 66 of the metallic foil are of similar lengths extending between the electrically conductive elements 61. The connecting portions 66 retain the electrically conductive elements 61 together and appropriately spaced apart until the electrically conductive elements 61 have been bonded to the catheter 5 by the adhesive backing 63.

To assemble the catheter 60, with the electrically conductive elements 61 formed in the sheet 62 of metallic foil and connected together by the connecting portions 66, the protective sheet 64 is removed from the adhesive backing 63, and the electrically conductive elements 61 connected by the connecting portions 66 are offered up to the catheter, with the connecting portions 66 extending longitudinally of the catheter 60. With the connecting portions 66 extending longitudinally of the catheter 60 and the electrically conductive elements 61 extending transversely thereof, the electrically conductive elements 61 and the connecting portions 66 are maneuvered axially along the catheter 60 until the electrically conductive elements 61 are located at the appropriate locations on the catheter 60 adjacent the corresponding radial communicating openings 12. The connecting portions 66 are then brought into contact with the catheter 60 and bonded thereto by the adhesive backing 63. The electrically conductive elements 61 are then wrapped around the catheter to form the band electrodes 5 with free ends 67 of the electrically conductive elements 61 abutting each other. The electrically conductive elements 61 are then severed from the adjacent connecting portions 66, which are removed from the catheter 60.

However, in certain cases, it is envisaged that the connecting portions 66 may be left on the catheter 60, but would be severed in order to break electrical continuity between the adjacent electrically conductive elements 61. The insulated electrically conductive wires 10 are then passed into the axial communicating bore 9 through the radial communicating openings 12 and are urged through the axial communicating bore 9 to the proximal end 3 of the catheter 1. Free ends of the wires 10 extending outwardly through the radial communicating openings 12 are skived and are electrically coupled to the outer surface 68 of the corresponding electrically conductive elements 61 by an electrically conductive adhesive 69 or by soldering or by other suitable electrical coupling means.

Although not illustrated, an axial medium accommodating bore similar to the axial medium accommodating bore 16 of the catheter 1 may be provided extending axially through the catheter 60 from the proximal end thereof towards the distal end, and a plurality of radial medium accommodating bores similar to the radial medium accommodating bores 17 of the catheter 1 may be provided extending from the axial medium accommodating bore through the catheter for accommodating a fluid into or out of the axial medium accommodating bore.

Otherwise, the catheter 60 is similar to the catheter 1, as is its use.

Referring now to FIG. 11, there is illustrated a plurality of electrically conductive elements 70 which have been formed from a sheet 71 of electrically conductive metallic foil of thickness of the order of 35 microns to 50 microns. The electrically conductive elements 70 are provided to form band electrodes similar to the electrodes 5 of the catheters described with reference to FIGS. 1 to 10, and for bonding to any one of the catheters of FIGS. 1 to 10. The foil sheet 71 is similar to the foil sheet 62 of FIGS. 9 and 10, and comprises an adhesive backing 73 which is protected by a protective releasable sheet 74. The electrically conductive elements 70 are joined by a plurality of connecting portions 75 which form an elongated connecting portion 76 from which the electrically conductive elements 70 extend transversely therefrom. The elongated connecting portion 76 retains the electrically conductive elements 70 together and appropriately spaced apart until the electrically conductive elements 70 have been bonded to the catheter.

In this embodiment of the invention prior to bonding the electrically conductive elements 70 to any one of the catheters of FIGS. 1 to 10, for example, the catheter 50 of FIGS. 5 and 6, a portion of the protective sheet 74 is peeled back from the free ends 77 of the electrically conductive elements 70, and the electrically conductive wires 10 are electrically coupled to respective corresponding ones of the electrically conductive elements 70 by the adhesive backing 73. The adhesive backing 73 is an electrically conductive contact adhesive in order to provide electrical continuity between the wires 10 and the corresponding electrically conductive elements 70. Alternatively, an additional electrically conductive adhesive as well as the adhesive backing 73 may be used to electrically couple the wires 10 to the corresponding electrically conductive elements 70. In a further alternative embodiment of the invention the electrically conductive wires 10 may be soldered or welded to the electrically conductive elements 70 adjacent the free ends thereof, however, in which case, the adhesive backing 73 would have to be removed from the electrically conductive elements 70 in respective local areas adjacent the solder or weld joints, in order to facilitate soldering or welding of the wires 10 to the electrically conductive elements 70.

On being electrically coupled to the electrically conductive elements 70, the wires 10 are then threaded through corresponding ones of the radial communicating openings 12 of the catheter 50 into the axial communicating bore 9 and in turn through the axial communicating bore 9 to the proximal end 3 of the catheter 50. When the wires 10 have been fully threaded through the radial communicating openings 12 and the first axial communicating bores 9, the free ends 77 of the electrically conductive elements 70 are initially brought into contact with the catheter 50 and bonded thereto by the adhesive backing 73. The portions of the protective sheet 74 on the electrically conductive elements 70 are then progressively peeled from the adhesive backing on the electrically conductive elements 70 towards the elongated connecting portion 74, and as the portions of the protective sheet 74 are being peeled from the adhesive backing 73, the electrically conductive elements 70 are progressively wrapped around the catheter 50, thereby progressively bringing the adhesive backing 73 of the electrically conductive elements 70 into contact with the catheter 50 for progressively bonding the electrically conductive elements 70 to the catheter 50. On the electrically conductive elements 70 being bonded to the catheter 50, and extending completely around the catheter 50 to form the electrodes 5, the electrically conductive elements 70 are then severed from the elongated connecting portion 76 in order to mutually isolate the electrodes. Since the wires 10 are electrically coupled to the electrically conductive elements 70 on the same side as the adhesive backing 73, the electrically conductive wires 10 are electrically coupled to the electrically conductive elements 70 on the underside thereof. Thus, the electrically conductive coupling joints between the wires 10 and the electrically conductive elements 70 are located within the respective radial communicating openings 12, thereby minimising projections from the catheter 50.

Referring now to FIGS. 12 and 13, there is illustrated a catheter according to another embodiment of the invention, indicated generally by the reference numeral 80. The catheter 80 is substantially similar to the catheter 1 and similar components are identified by the same reference numerals. The main difference between the catheter 80 and the catheter 1 is that in this embodiment of the invention the electrodes 5 are formed by electrically conductive elements 81 which are machined from a single elongated hollow cylinder 82 of electrically conductive semi-rigid metallic material. The cylinder 82 is machined so that the electrically conductive elements 81 are in the form of endless bands, which are joined by connecting portions 83 of the cylinder 82 for facilitating assembly of the electrically conductive elements 81 onto the catheter 80. The internal diameter of the cylinder 82 corresponds to the external diameter of the catheter 80, so that the electrically conductive elements 81 are a tight sliding fit on the catheter 80. When formed, the electrically conductive elements 81 while still joined by the connecting portions 83 are slid over the catheter 80 and positioned with the electrically conductive elements 81 located adjacent the corresponding radial communicating openings 12, so that electrically conductive wires 10 can subsequently be electrically coupled to outer surface 84 of the electrically conductive elements 81 by an electrically conductive adhesive or by soldering or welding. Once positioned on the catheter 80, the electrically conductive elements 81 are bonded and/or crimped onto the catheter 80, and the connecting portions 83 are severed and removed for mutually insulating the electrodes 81. The connecting portions 83 may be severed or removed completely by any suitable means, for example, chemical etching or the like. The wires 10 are then passed through the radial communicating openings 12 into the axial communicating bore 9, and urged along the bore 9 to the proximal end 3 of the catheter 80. The distal ends of the wires 10 are skived and electrically coupled to the corresponding electrically conductive elements.

In this embodiment of the invention the metallic material of the cylinder, while it is semi-rigid, nonetheless is deformable for facilitating crimping of the electrically conductive elements 81 onto the catheter 80.

Otherwise, the catheter 80 is similar to the catheter 1.

Referring now to FIG. 14, there is illustrated a catheter according to a still further embodiment of the invention, indicated generally by the reference numeral 90. The catheter 90 is substantially similar to the catheter 1, and similar components are identified by the same reference numerals. However, in this embodiment of the invention the mutually insulated electrically conductive wires 10 instead of extending through an axial communicating bore 9 are integrally moulded or extruded, and typically extruded with the material of the catheter 90 in a wall 91 thereof, and extend through the wall 91 around the catheter 90 in the form of a long pitch helix. Contact is made with the wires 10 by skiving respective portions 92 of the wall 91 of the catheter 90 adjacent locations where electrodes 5 are to be provided. The wires 10 when located in the skived portions 92 of the catheter 90 may be either pulled out of the catheter 90 through the skived portions 92 by pulling the distal portion of the wires 10 through the skived portions 92, and then the corresponding wires 10 may be electrically coupled to the adjacent electrodes 5 by an electrically conductive adhesive or by soldering or welding. Alternatively, the skived portion 92 of the catheter 90 may be filled with solder or an electrically conductive adhesive so that when the electrodes 5 are secured to the catheter 90, the electrodes make electrical contact with the corresponding wires 10 through the adhesive or solder formed in the skived portions 92. In this embodiment of the invention the electrodes 5 are illustrated in broken lines extending over the skived portions 92 where electrical contact is made between the electrodes 5 and the corresponding wires 10 through the electrically conductive adhesive or solder formed in the skived portions 92 of the catheter 90.

The electrodes 5 may be any suitable electrodes, band type or otherwise, and if band type electrodes, may be provided in the form of the electrodes of any of the catheters described with reference to FIGS. 1 to 13.

As can be seen in this embodiment of the invention, an axial medium accommodating bore 16 extends axially through the catheter 90 and is closed at its distal end, and radial medium accommodating bores 17 extend through the wall 91 of the catheter 90 between the electrodes 5 and between the wires 10 into the axial medium accommodating bore 16 for accommodating fluid into or out of the second axial communicating bore 16.

Otherwise, the catheter 90 is similar to the catheter 1.

Referring now to FIGS. 15 to 23, there is illustrated a catheter according to a further embodiment of the invention, indicated generally by the reference numeral 100, which is produced by a method according to another embodiment of the invention, which will be described in detail below. The catheter 100 is substantially similar to the catheter 1, and similar components are identified by the same reference numerals. The catheter 100 according to this embodiment of the invention is particularly suited for use in determining transverse cross-sectional dimensions of a vessel, cavity, lumen or the like into which the catheter 1 is introduced. The catheter 1 is also particularly suitable for use in conjunction with an inflatable element located around the catheter of the type which will be described in more detail below, with reference to FIGS. 24 and 25.

Referring now in particular to FIG. 15, the catheter 100 is of an extruded polymer material, and extends between a proximal end 3 and a distal end 4. A plurality of spaced apart electrodes 5, namely, two stimulating electrodes 101 and seventeen receiving electrodes 102 are bonded to the catheter 100 adjacent its distal end 4. The electrodes 5 are of electrically conductive metal foil material and extend completely around the catheter 100 with respective opposite ends of the electrodes 5 abutting each other.

Referring now to FIGS. 16 to 23, an axial communicating bore 9 extending longitudinally through the catheter 100 from the proximal end 3 to the distal end 4 accommodates a loom 103 of the mutually insulated electrically conductive wires 10 from the proximal end 3 to the electrodes 5 for individually coupling the respective electrodes 5 to remote electronic control and analysing apparatus (not shown) provided externally and independently of the catheter 100 for applying stimulating signals to the stimulating electrodes 101 and analysing resulting signals produced on the receiving electrodes 102 in response to the stimulating signal for determining characteristics of a vessel, cavity or lumen in which the distal end 4 of the catheter 100 is located as will be briefly described below. One insulated wire 10 is provided for each electrode 5, and thus, nineteen wires 10 are provided in the loom 103 for the electrodes 5.

A portion of the axial communicating bore 9 extends through the catheter 100 relatively closely to the outer circumferential surface 6 of the catheter 100 at one portion thereof for facilitating the formation of a single radial communicating opening, which in this case is a longitudinally extending elongated communicating slot 105 for accommodating the loom 103 of the wires 10 therethrough from the axial communicating bore 9 for electrically coupling the wires 10 to the respective corresponding electrodes 5.

A first axial medium accommodating bore 16 extends through the catheter 100 from the proximal end 3 to the distal end 4 for delivering an electrically conductive fluid into the vessel, cavity or lumen within which the distal end 4 of the catheter 100 is located. A pair of spaced apart first radial medium accommodating bores 17 extending radially through the catheter 100 communicate with the first axial medium accommodating bore 16 for accommodating fluid from the first axial medium accommodating bore 16 into the vessel, cavity or lumen in which the distal end 4 of the catheter 100 is located, or vice versa.

A second axial medium accommodating bore 106 extends longitudinally through the catheter 100 from the proximal end 3 to the distal end 4, and a pair of second radial medium accommodating bores 107 extending radially through the catheter 100 communicates the second axial medium accommodating bore 106 with the vessel, cavity or lumen in which the distal end 4 of the catheter 100 is located. The second axial medium accommodating bore 106 may be used for monitoring the pressure of fluid pumped into the vessel, cavity or lumen in which the distal end 4 of the catheter 100 is located by using suitable pressure monitoring apparatus located at the proximal end 3 of the catheter 100 or remotely therefrom. Ends of the axial communicating bore 9 and the first and second medium accommodating bores 16 and 106 adjacent the distal end 4 of the catheter 100 are sealed by a suitable sealant, a plug or a closure cap, or by melting the distal end 4 of the catheter 100. The end of the axial communicating bore 9 at the proximal end of the catheter 100 with the wires 10 extending therethrough is also sealed.

Referring now to FIGS. 16 to 23, the method for producing the catheter 100 will now be described. The electrodes 5 are formed from a single sheet 110 of the electrically conductive metal foil material, typically, of thickness of the order of 35 microns to 50 microns. In this embodiment of the invention the sheet 110 is not provided with an adhesive backing. Slots 111 are formed in the sheet 110 to define electrically conductive elements 114, which in turn form the electrodes 5, extending between respective elongated side connecting portions 112 and 113. The slots 111 define the electrically conductive elements 114 extending parallel to each other. The side connecting portions 112 and 113 act to retain the electrically conductive elements 114 together and appropriately spaced apart from each other until the electrically conductive elements have been bonded to the catheter 100. The electrically conductive elements 114 which form the receiving electrodes 102 are retained equi-spaced apart from each other, and the electrically conductive elements 114 which form the stimulating electrodes 101 are retained spaced apart from the respective adjacent receiving electrodes 102 a distance greater than the spacing between the receiving electrodes 102, although the spacing between the stimulating electrodes 101 and the adjacent receiving electrodes 102 may be equal to or less than the spacing between the receiving electrodes 102. The length of the electrically conductive elements 114 between the side connecting portions 112 and 113 is such that the electrically conductive elements 114 extend completely around the catheter 100 with free ends 115 thereof abutting each other, although if desired, the electrically conductive elements 114 could be of length such that the free ends 115 thereof overlap when wrapped around the catheter 100.

After the electrically conductive elements 114 extending between the connecting portions 112 and 113 have been formed by the slots 111, the wires 10 are electrically coupled to the electrically conductive elements 114 intermediate the free ends 115 thereof, and substantially centrally relative to the free ends 115. The electrical coupling of the wires 10 to the electrically conductive elements 114 may be by soldering, by an electrically conductive adhesive, by induction welding or the like. The wires 10 are soldered, welded or bonded to the electrically conductive elements 114 so that the coupling joint is located on the underside 116 thereof when the electrically conductive elements 114 are bonded to the catheter 100.

With the wires 10 electrically coupled to the electrically conductive elements 114, two elongated pieces of double-sided adhesive tape 118 are secured to the electrically conductive elements 114 on respective opposite sides of the locations at which the wires 70 are electrically coupled to the electrically conductive elements 114, and between the wires 10 and the respective free ends 115 of the electrically conductive elements 114. The double-sided tapes 118 are secured to the electrically conductive elements 114 extending parallel to the connecting portions 112 and 113, and with the electrodes 5 extending transversely of the tapes 118. The double-sided tapes 118 are provided with protective releasable sheets extending on respective opposite faces of the tapes 118 for protecting the adhesive on the respective opposite faces thereof. Only one of the protective sheets is removed from each of the tapes 118 as the tapes 118 are being secured to the electrically conductive elements 114. The remaining protective sheet, namely, the protective sheet 119 on each of the tapes 118 is not removed until the electrically conductive elements 114 are about to be bonded to the catheter 100.

The wires 10 having been electrically coupled to the electrically conductive elements 114 are next inserted into the axial communicating bore 9 through the communicating slot 105, and are urged through the axial communicating bore 9 until they extend outwardly thereof through the proximal end 3. With the wires 10 extending through the communicating slot 105, and with the double-sided adhesive tapes 118 secured to the electrically conductive elements 114, the electrically conductive elements 114 are located on the catheter 100 extending transversely of the communicating slot 105 with the side connecting portions 112 and 113 extending parallel to the catheter 100. The remaining protective sheets 119 are then removed from the double-sided adhesive tapes 118 and the electrically conductive elements 114 are wrapped around the catheter 100 on respective opposite sides of the communicating slot 105, and are bonded to the catheter 100 by the double-sided adhesive tapes 118.

The electrically conductive elements 114 are then severed from the respective connecting portions 112 and 113 adjacent the free ends 115 thereof. The portion of the respective tapes 118 adjacent the free ends 115 of the electrically conductive elements 114 along with the free ends 115 of the electrically conductive elements 114 are urged into engagement with the catheter 101 for securing the free ends 115 thereof to the catheter 100. As discussed above, the length of the electrically conductive elements 114 between their respective free ends 115 is such that when the free ends 115 are secured to the catheter 100 by the double-sided adhesive tapes 118, the free ends 115 of the electrically conductive elements 114 abut each other to form the electrodes 5 as band electrodes. Since the electrodes 5 have been severed from the respective connecting members 112 and 113, the electrodes 5 are mutually insulated from each other. In this embodiment of the invention both the double-sided adhesive tapes 118 and the adhesives thereof are non-electrically conductive in order to ensure mutual insulation of the electrodes 5.

In an alternative method for bonding the electrically conductive elements 114 to the catheter 100, the wires 10 are initially inserted into the axial communicating bore 9 through the communicating slot 105 and urged along the axial communicating bore 9 to extend through the proximal end 3 thereof. The distal portions of the wires 10 extending outwardly through the communicating slot 105 are then electrically coupled to the respective electrically conductive elements 114, which at this stage are provided with the respective double-sided tapes 118 located thereon extending parallel to the respective side connecting portions 112 and 113. The wires 10 are then further pulled through the axial communicating bore 9 from the proximal end thereof, thereby urging the electrically conductive elements 114 towards the catheter 100 adjacent the communicating slot 105. By further manipulation of the wires 10 and the electrically conductive elements 114, the electrically conductive elements 114 are located in the desired respective locations on the catheter 100 and are located extending transversely of the communicating slot 105.

The protective sheet 119 is then progressively removed from one of the double-sided adhesive tapes 118 and the portions of the electrically conductive elements 114 adjacent that double-sided adhesive tape 118 are progressively wrapped around the catheter, thereby progressively urging the double-sided adhesive tape 118 into engagement with the catheter for bonding the corresponding portions of the electrically conductive elements 114 to the catheter. The adjacent side connection portion 112 or 113 is then severed from the electrically conductive elements 114. The protective sheet 119 of the other double-sided adhesive tape 118 is then progressively removed from the remaining double-sided adhesive tape 118, and the remaining portions of the electrically conductive elements 114 are progressively wrapped around the catheter 100, thereby progressively urging the corresponding double-sided adhesive tape 118 into bonding engagement with the catheter 100 for bonding the corresponding portions of the electrically conductive elements 114 to the catheter 100. Prior to bonding the free ends of the remaining portions of the electrically conductive elements 114 to the catheter 100, the remaining one of the side connecting portions 112 and 113 is severed from the electrically conductive elements 114, and the free ends of the electrically conductive elements 114 are then urged towards the catheter, for bonding thereof with the adjacent double-sided adhesive tape 118. Since, as discussed above, the electrically conductive elements 114 are of length to extend completely around the catheter 100 with the respective free ends of each electrically conductive element abutting each other, once the remaining free ends of the electrically conductive elements 114 have been bonded to the catheter 100 by the corresponding double-sided adhesive tape 118, the respective free ends of each electrically conductive element 114 abut each other so that the electrically conductive elements 114 form band type electrodes extending completely around the catheter 100.

The portions of the double-sided adhesive tapes 118 intermediate the electrodes 5, in general, is left on the catheter. However, if desired, the portions of the double-sided adhesive tapes 118 intermediate the electrodes 5 could be removed.

Alternatively, if desired, instead of applying the double-sided adhesive tapes 118 initially to the electrically conductive elements 114, the double-sided adhesive tapes 118 could instead be initially applied to the catheter 100 extending longitudinally on respective opposite sides of the communicating slot 105, and the electrically conductive elements 114 would then be secured to the double-sided tapes 118 as the electrically conductive elements 114 are being simultaneously wrapped around the catheter 100.

It is also envisaged that instead of securing the electrically conductive elements 114 to the catheter 100 by double-sided adhesive tapes 118, the electrically conductive elements 114 could be secured to the catheter 100 by an adhesive, which could be applied directly to the underside of the electrically conductive elements 114 or to the outer surface 6 of the catheter 100. Indeed, in certain cases, it is envisaged that openings may be provided in the electrically conductive elements 114 at suitable locations intermediate the locations at which the wires 10 are secured to the electrically conductive elements 114 and the free ends 115 thereof for facilitating injecting a suitable adhesive therethrough between the electrically conductive elements 114 and the outer surface 6 of the catheter 100.

Turning now to the catheter 100, the catheter 100 is extruded, and the axial communicating bore 9 as well as the first and second axial medium accommodating bores 16 and 106 are formed as the catheter 1 is being extruded. The bores 9, 16 and 106 are formed so that respective portions of the bores 9 and 106 along their lengths at locations 120, 121 and 123, respectively, are located relatively closely to the outer surface 6 of the catheter 100. After extrusion, the elongated communicating slot 105 is formed towards the distal end 4 of the catheter 100, so that the communicating slot 105 communicates directly with the axial communicating bore 9. The communicating slot 105 may be formed by machining through the portion 120 of the catheter 100 by a suitable implement, or by skiving a portion of the catheter 100 at 120 until the axial communicating bore 9 is exposed, or by any other suitable process, such as thermal ablation, laser ablation or the like.

Where the catheter 100 is to be used for determining dimensional characteristics of a vessel, a cavity or lumen, for example, a blood vessel such as an artery, a cavity, for example, a heart cavity, or a lumen, for example, the oesophagus or the like, the catheter 100 is appropriately introduced into the vessel, cavity or lumen so that the distal end 4 is located in the vessel, cavity or lumen. A suitable fluid, which may, for example, be an electrically conductive liquid, such as a saline solution is then pumped through the first axial medium accommodating bore 16 to fill the vessel, cavity or lumen. The pressure of the saline solution in the vessel, cavity or lumen is monitored by monitoring the pressure of the saline solution in the second axial medium accommodating bore 106.

Stimulus current signals of known current value are applied by the electronic control and analysing apparatus (not shown) to the stimulating electrodes 101, and resulting voltage signals on the receiving electrodes 102 in response to the stimulus current signals on the stimulating electrodes 101 are read by the control and analysing apparatus for determining the electrical impedance in the saline solution between the stimulating electrodes 101 and the receiving electrodes 102, and between adjacent ones of the receiving electrodes 102, which in turn permits a determination of the transverse cross-sectional area of the vessel, cavity or lumen to be determined adjacent the respective receiving electrodes 102. The use of such catheters for determining dimensional characteristics of a vessel, cavity or lumen will be well known to those skilled in the art.

Referring now to FIGS. 24 and 25, there is illustrated a balloon catheter also according to the invention, indicated generally by the reference numeral 130. The balloon catheter 130 comprises a catheter 131 which is identical to the catheter 100, and similar components are identified by the same reference numerals. An expandable element comprising an inflatable balloon 132 is secured to the catheter 131 adjacent the distal end 4 thereof and extends completely around the catheter 131 to define with the catheter 131 a hollow interior region in the form of an annulus 133. The stimulating electrodes 101 and the receiving electrodes 102 are located on the catheter 131 within the annulus 133. The first and second axial medium accommodating bores 16 and 106 communicate with the annulus 133 through the first and second radial medium accommodating bores 17 and 107, respectively. The balloon 132 is inflatable by delivering an electrically conductive inflating medium, which typically, is a saline solution, when it is desired to determine measurement characteristics such as transverse cross-sectional area, diameter and volume of a vessel, cavity or lumen within which the balloon 132 of the balloon catheter 130 is located. Inflating of the balloon 132 to define the transverse cross-section of the vessel, cavity or lumen is carried out by pumping the saline solution into the annulus 133 through the first axial medium accommodating bore 16. The pressure of the saline solution in the annulus 133 is monitored during inflating of the balloon 132 by a pressure sensor (not shown), which monitors the pressure in the saline solution in the second axial medium accommodating bore 106. On the balloon 132 being inflated to the appropriate pressure to abut the side wall of the vessel, cavity or lumen within which the balloon 132 is located, the dimensional characteristics of the vessel, cavity or lumen are determined by applying a stimulus current signal of known current value to the stimulating electrodes 101 and reading the resulting voltage signals on the receiving electrodes 102, as has already been described with reference to the catheter 100.

In this embodiment of the invention the balloon 132 and the catheter 131 are coated with a low friction coating 134 for facilitating urging of the balloon catheter 130 through a working channel of, for example, an endoscope or the like. In this embodiment of the invention the low friction coating is of a hydrophilic material, namely, Parylene, which is plasma deposited to a depth of approximately 0.5 microns to 2 microns on the external surface of the balloon 132 and the catheter 131. However, coating of the balloon 132 and/or the catheter 131 with a low friction coating is not essential.

While the catheters according to the invention have been described for determining dimensions of characteristics of a vessel, cavity or lumen, the catheters and the balloon catheter may be used for other purposes. In particular, the balloon catheter may be used for dilating a lumen or dilating an obstruction in a lumen, vessel or cavity by inflation thereof, and the degree of dilation would be monitored by determining the dimensional characteristics of the balloon as the obstruction or otherwise is being dilated. Alternatively, the catheters may be used for ablating tissue by appropriately applying suitable high power radio frequency signals to the electrodes 5. For example, the balloon catheter may be used for ablating tissue, for example, tissue in a vessel, cavity or lumen, such as, for example, the oesophagus or the like. In which case, it is envisaged that two electrodes would be sufficient for ablating the tissue, and the two ablating electrodes would be located on the outer circumferential surface of the balloon.

Needless to say, the uses to which the catheters and the balloon catheter may be put are many, and will be readily apparent to those skilled in the art.

The catheters according to the invention are of a construction which particularly lends itself to catheters of relatively small diameter, typically of outer diameter of, for example, 2 mm to 7 mm, and also the construction of the catheters according to the invention is particularly suitable for catheters in which a relatively large number of axially spaced apart electrodes of relatively small axial width are required, for example, electrodes of 1 mm to 5 mm axial wide, with correspondingly dimensioned axial spacing therebetween. Additionally, the catheters according to the invention can be produced of a relatively flexible polymer material, and the provision of the electrodes on the catheter do not to any great extent affect the flexibility of the catheter.

In the embodiments of the invention described, while the electrically conductive tape, foil and metal are of relatively small thickness, and typically, of thickness of the order of 35 microns to 50 microns, the electrically conductive tape, foil and metal may be of thickness up to 200 microns. By providing the electrodes as being of electrically conductive tape, foil or metal of such thickness, the electrodes add little to the overall diameter of the catheters, and furthermore, do not provide obstructive steps as the catheter is being passed through a hollow organ, vessel, lumen or the like. Indeed, the catheters are of a particularly desirable construction, since they minimise the overall outer diameter of the catheter adjacent the electrodes, and furthermore, in many of the catheters according to the invention, the wires are completely concealed within the catheter.

While the catheters according to the invention have been described as comprising first and second axial and radial medium accommodating bores for accommodating a fluid therethrough, in certain cases, the first and second axial and radial medium accommodating bores or at least one of the first and second axial and radial medium accommodating bores may be omitted. Indeed, more than two axial medium accommodating bores may be provided, and furthermore, many more radial medium accommodating bores may be provided for each axial medium accommodating bore, in order to facilitate rapid and even filling of the balloon with the inflating medium.

The electrodes of the catheters according to the invention may be coupled to electronic control and analysing apparatus in any suitable or desired configuration. For example, it is envisaged that some of the electrodes may be coupled to be configured as stimulating electrodes, and others would be coupled to be configured as receiving electrodes. Typically, a stimulating voltage or current would be applied to the stimulating electrodes, and the resulting voltages or currents on the receiving electrodes would be read by the electronic control and analysis apparatus. When so configured, the catheter would be suitable for measuring the volume and/or diameters of a cavity along the axial length of the catheter. In such cases, in general, the two outermost electrodes would be configured to be stimulating electrodes, and the remaining electrodes between the two outermost electrodes would be configured to be receiving electrodes.

In general, it is envisaged that the catheters or at least that portion of the catheters onto which the electrodes are secured will be of a non-electrically conductive material, for example, a plastics material, a polymer or the like.

While the electrodes have been described as being band type electrodes which extend completely around the catheter, it is envisaged that in certain cases, the electrodes may not extend completely around the catheter.

Furthermore, while the electrically conductive inflating medium has been described as a saline solution, any other suitable electrically conductive medium may be used where it is desired that the inflating medium of the balloon be electrically conductive.

While the balloon has been described as being of cylindrical configuration when inflated, the balloon may be of any other shape, and may be of any other transverse cross-section besides circular. For example, the balloon when inflated may be of square, rectangular, triangular, hexagonal, polygonal or any other desired transverse cross-section, and in certain cases, it is envisaged that the transverse cross-section of the balloon may be matched to the cross-section of the lumen or cavity into which they are to be inserted.

While a plurality of wires have been described extending through the catheter for coupling the respective electrodes to control and analysing apparatus, it is envisaged in certain cases that the number of wires extending through the catheter may be reduced by multiplexing some or all of the signals from the receiving electrodes onto one or more wires. The multiplexing could be carried out by a multiplexer located in the balloon or in the catheter adjacent the electrodes.

The invention claimed is:

1. A method for producing a catheter with a plurality of spaced apart electrodes thereon, the method comprising:
   forming the electrodes from respective electrically conductive elements, the electrically conductive elements being formed from a single sheet of electrically conductive material with the electrically conductive elements being spaced apart from each other and being joined by connecting portions formed by portions of the single sheet of electrically conductive material between the electrically conductive elements, the electrically conductive elements being of length sufficient to extend at least partly around the catheter,
   bonding the electrically conductive elements to the catheter with the electrically conductive elements being joined by the connecting portions and extending at least partly around the catheter, and
   severing each connecting portion from at least one of the electrically conductive elements which are joined by the connecting portion subsequent to the electrically conductive elements being bonded to the catheter to form the electrodes thereon.

2. A method as claimed in claim 1 in which the electrically conductive elements are bonded to the catheter by progressively wrapping the electrically conductive elements around the catheter.

3. A method as claimed in claim 1 in which the single sheet of the electrically conductive material comprises a single sheet of electrically conductive foil material.

4. A method as claimed in claim 3 in which the connecting portions extend between the respective adjacent ones of the electrically conductive elements intermediate the ends thereof.

5. A method as claimed in claim 1 in which each electrically conductive element is electrically coupled to a corresponding electrically conductive wire.

6. A method as claimed in claim 5 in which a plurality of the spaced apart electrically conductive elements are bonded to the catheter by at least one elongated piece of double-sided adhesive tape.

7. A method as claimed in claim 5 in which an axial communicating bore is formed in the catheter extending from a proximal end thereof to a location adjacent the electrodes for accommodating the electrically conductive wires from the electrodes to the proximal end of the catheter, and at least one radial communicating opening is formed extending through the catheter adjacent the electrodes for accommodating the electrically conductive wires from the electrodes into the axial communicating bore.

8. A method as claimed in claim 5 in which each electrically conductive wire is electrically coupled to the surface of the corresponding electrically conductive element remote from the catheter subsequent to the electrically conductive element being bonded to the catheter.

9. A method as claimed in claim 1 in which each electrically conductive element is of length sufficient to form the corresponding electrode as a band electrode extending completely around the catheter.

10. A method as claimed in claim 1 in which each electrically conductive element is bonded to the catheter by an adhesive.

11. A method as claimed in claim 1 in which the electrically conductive elements are bonded to the catheter by a double-sided adhesive tape.

12. A method as claimed in claim 11 in which the double-sided adhesive tape is bonded to the corresponding electrically conductive element prior to bonding to the catheter.

13. A method as claimed in claim 1 in which the connecting portions form an elongated connecting portion, and the electrically conductive elements extend transversely from the elongated connecting portion at spaced apart intervals therefrom.

14. A method as claimed in claim 1 in which a pair of spaced apart elongated connecting portions are provided and the electrically conductive elements extend transversely between the elongated connecting portions.

15. A method as claimed in claim 5 in which each electrically conductive element is coupled to the corresponding electrically conductive wire prior to the electrically conductive element being bonded to the catheter.

16. A method as claimed in claim 5 in which each electrically conductive element is coupled to the corresponding electrically conductive wire subsequent to the electrically conductive element being bonded to the catheter.

17. A method as claimed in claim 6 in which the at least one elongated piece of double-sided adhesive tape is located on the electrically conductive elements to at least one side of the locations at which the corresponding electrically conductive wires are coupled thereto.

18. A method as claimed in claim 6 in which two elongated pieces of the double-sided adhesive tape are located on the electrically conductive elements on respective opposite sides of the locations at which the corresponding electrically conductive wires are coupled to the electrically conductive elements.

19. A method as claimed in claim 6 in which the respective electrically conductive elements extend transversely relative to each elongated piece of double-sided adhesive tape.

20. A method as claimed in claim 1 in which each electrically conductive element is of length sufficient to form the corresponding electrode as a band electrode extending completely around the catheter with one end of the electrically conductive element overlapping the opposite end thereof.

* * * * *